(12) United States Patent
Mehta et al.

(10) Patent No.: US 12,011,357 B2
(45) Date of Patent: Jun. 18, 2024

(54) ANATOMIC IMPLANT FOR JOINTS

(71) Applicant: Howmedica Osteonics Corp., Mahwah, NJ (US)

(72) Inventors: Ashish Mehta, Rajasthan (IN); Lance N. Terrill, Rochestown (IE)

(73) Assignee: Howmedica Osteonics Corp., Mahwah, NJ (US)

( * ) Notice: Subject to any disclaimer, the term of this patent is extended or adjusted under 35 U.S.C. 154(b) by 152 days.

(21) Appl. No.: 17/366,381

(22) Filed: Jul. 2, 2021

(65) Prior Publication Data

US 2022/0000629 A1    Jan. 6, 2022

Related U.S. Application Data

(60) Provisional application No. 63/048,271, filed on Jul. 6, 2020.

(51) Int. Cl.
*A61F 2/40* (2006.01)
*A61F 2/30* (2006.01)

(52) U.S. Cl.
CPC ........ *A61F 2/4081* (2013.01); *A61F 2/30771* (2013.01); *A61F 2002/30253* (2013.01); *A61F 2002/30322* (2013.01); *A61F 2002/30326* (2013.01); *A61F 2002/30383* (2013.01); *A61F 2002/30518* (2013.01);
(Continued)

(58) Field of Classification Search
CPC ...... A61F 2/28; A61F 2/30; A61F 2/32; A61F 2/38; A61F 2/389; A61F 2/40; A61F 2/4081; A61F 2/44; A61F 2002/30858; A61F 2002/30863; A61F 2002/30878;
(Continued)

(56) References Cited

U.S. PATENT DOCUMENTS

| 4,261,062 | A | 4/1981 | Amstutz et al. |
| 5,702,447 | A | 12/1997 | Walch et al. |

(Continued)

FOREIGN PATENT DOCUMENTS

| CA | 2627551 A1 | 5/2007 |
| EP | 1509161 B1 | 5/2009 |

(Continued)

OTHER PUBLICATIONS

European Search Report issued in Appln. No. 21183832.1 dated Dec. 13, 2021. (3 pages).

(Continued)

*Primary Examiner* — Sarah W Aleman
(74) *Attorney, Agent, or Firm* — Lerner David LLP

(57) ABSTRACT

One embodiment of the present disclosure relates to a glenoid implant with a body and a keel. The body includes an articulation surface and a bone facing surface, and the keel has a depth that extends from the bone facing surface to a free end of the keel. The keel has a first length and a first width, both measured in a plane perpendicular to a direction of the depth. The first length is measured perpendicular to the first width and is defined by a first distance from an inferior end of the keel to a superior end of the keel. The first width is measured at a first location adjacent to the inferior end, and the keel has a width dimension along a first portion of the keel from the first location to the superior end that tapers from the first location toward the superior end.

19 Claims, 18 Drawing Sheets

(52) U.S. Cl.
CPC .............. *A61F 2002/30593* (2013.01); *A61F 2002/30594* (2013.01); *A61F 2002/30818* (2013.01); *A61F 2002/30878* (2013.01)

(58) Field of Classification Search
CPC .. A61F 2002/30253; A61F 2002/30324; A61F 2002/30329; A61F 2002/30331
See application file for complete search history.

(56) References Cited

U.S. PATENT DOCUMENTS

| | | | |
|---|---|---|---|
| 6,699,289 B2 | 3/2004 | Iannotti et al. | |
| 7,831,292 B2 | 11/2010 | Quaid et al. | |
| 7,892,287 B2 | 2/2011 | Deffenbaugh | |
| 8,080,063 B2 | 12/2011 | Ferrand et al. | |
| 8,241,367 B2 | 8/2012 | Justin et al. | |
| 8,556,980 B2 | 10/2013 | Deffenbaugh | |
| 8,690,951 B2 | 4/2014 | Baum et al. | |
| 8,721,727 B2 | 5/2014 | Ratron et al. | |
| 8,778,028 B2 * | 7/2014 | Gunther | A61B 17/15 623/19.11 |
| 8,870,962 B2 * | 10/2014 | Roche | A61F 2/40 623/19.12 |
| 8,882,845 B2 * | 11/2014 | Wirth | A61F 2/4081 623/19.13 |
| 8,998,990 B2 * | 4/2015 | Bertagnoli | A61B 17/144 623/17.16 |
| 9,381,085 B2 | 7/2016 | Axelson, Jr. et al. | |
| 9,474,619 B2 | 10/2016 | Reubelt et al. | |
| 9,763,798 B2 | 9/2017 | Chavarria et al. | |
| 9,814,471 B2 | 11/2017 | Goldberg et al. | |
| 10,342,669 B2 * | 7/2019 | Hopkins | A61F 2/4081 |
| 10,537,441 B2 | 1/2020 | Axelson, Jr. et al. | |
| 10,583,014 B2 | 3/2020 | Bertagnoli et al. | |
| 2005/0049709 A1 * | 3/2005 | Tornier | A61F 2/4081 623/19.13 |
| 2005/0261775 A1 | 11/2005 | Baum et al. | |
| 2006/0142657 A1 | 6/2006 | Quaid et al. | |
| 2007/0016304 A1 | 1/2007 | Chudik | |
| 2007/0142917 A1 | 6/2007 | Roche et al. | |
| 2007/0244564 A1 * | 10/2007 | Ferrand | A61F 2/4081 623/19.13 |
| 2009/0125113 A1 | 5/2009 | Guederian et al. | |
| 2010/0228352 A1 * | 9/2010 | Courtney, Jr. | A61F 2/4081 606/301 |
| 2011/0224673 A1 | 9/2011 | Smith | |
| 2013/0144393 A1 * | 6/2013 | Mutchler | A61F 2/4081 623/19.11 |
| 2013/0150975 A1 | 6/2013 | Tannotti et al. | |
| 2014/0188132 A1 | 7/2014 | Kang | |
| 2015/0080717 A1 | 3/2015 | Ferko | |
| 2015/0081030 A1 | 3/2015 | Zubok et al. | |
| 2015/0119987 A1 | 4/2015 | Davignon et al. | |
| 2015/0272741 A1 | 10/2015 | Taylor et al. | |
| 2017/0000562 A1 | 1/2017 | Frank et al. | |
| 2017/0014238 A1 | 1/2017 | Reubelt et al. | |
| 2017/0239058 A1 | 8/2017 | Goldberg | |
| 2017/0319348 A1 | 11/2017 | Goldberg | |
| 2017/0360456 A1 | 12/2017 | Gunther | |
| 2018/0280151 A1 | 10/2018 | Humphrey | |
| 2019/0076261 A1 | 3/2019 | Mutchler et al. | |
| 2020/0015830 A1 | 1/2020 | Bonin, Jr. et al. | |
| 2020/0261232 A1 | 8/2020 | Mistry | |

FOREIGN PATENT DOCUMENTS

| | | |
|---|---|---|
| EP | 2057970 B1 | 1/2016 |
| EP | 2968655 B1 | 12/2018 |
| WO | 2007051151 A2 | 5/2007 |

OTHER PUBLICATIONS

Carpenter et al., Porous metals and alternate bearing surfaces in shoulder arthroplasty, Curr Rev Musculoskelet Med, Published online Jan. 2016, pp. 59-66.

Iannotti et al., The Normal Glenohumeral Relationships, An Anatomical Study of One Hundred and Forty Shoulders, The Journal of Bone and Joint Surgery, Inc., Apr. 1992, pp. 491-500, vol. 74-A, No. 4.

Lance N. Terrill, U.S. Appl. No. 62/873,266, filed Jul. 12, 2019, titled "Augmented Glenoid Design".

Schrumpf, et al., The glenoid in total shoulder arthroplasty, Current Reviews in Musculoskeletal Medicine, published online Aug. 2011, pp. 191-199, vol. 4.

* cited by examiner

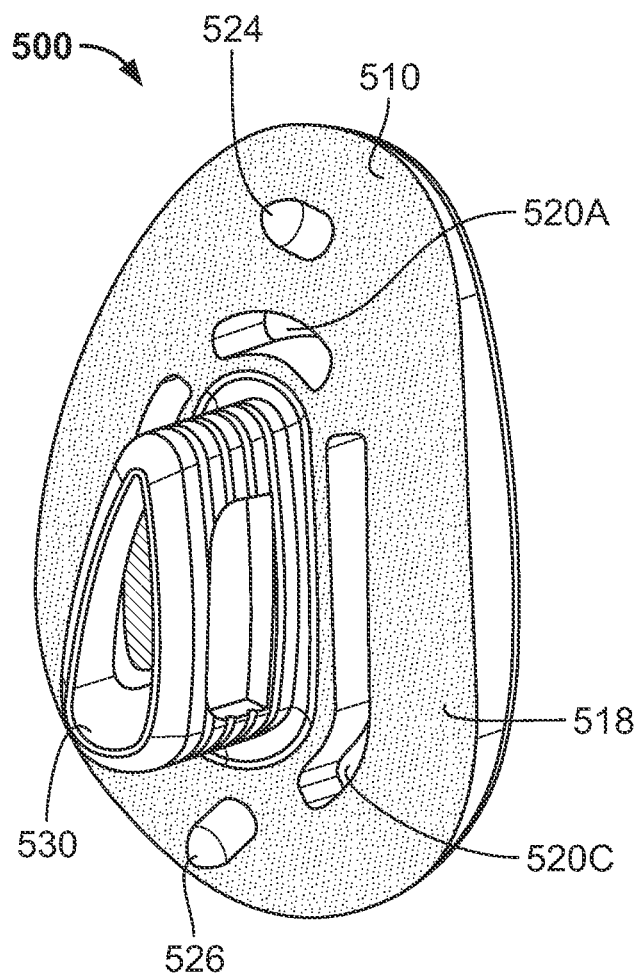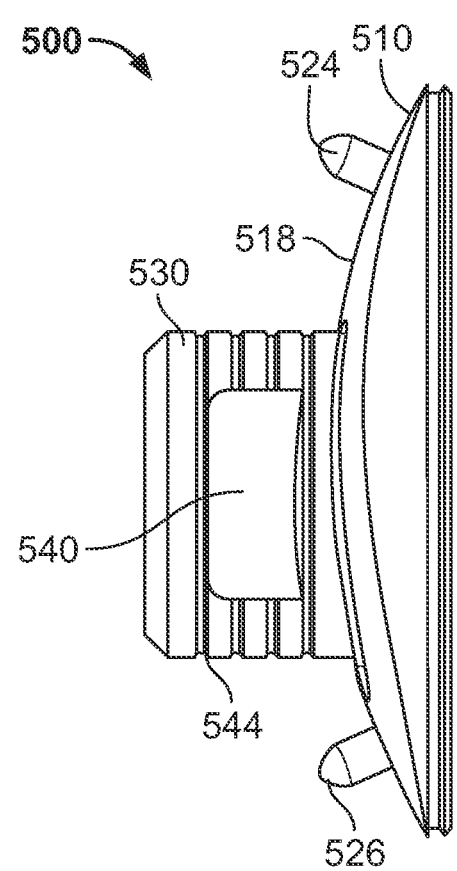
FIG. 13
FIG. 14

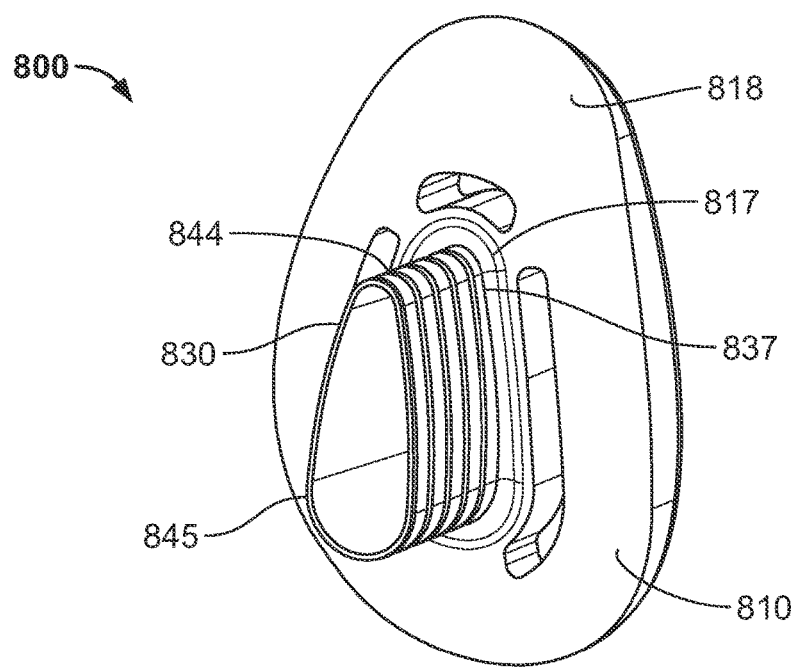
FIG. 19
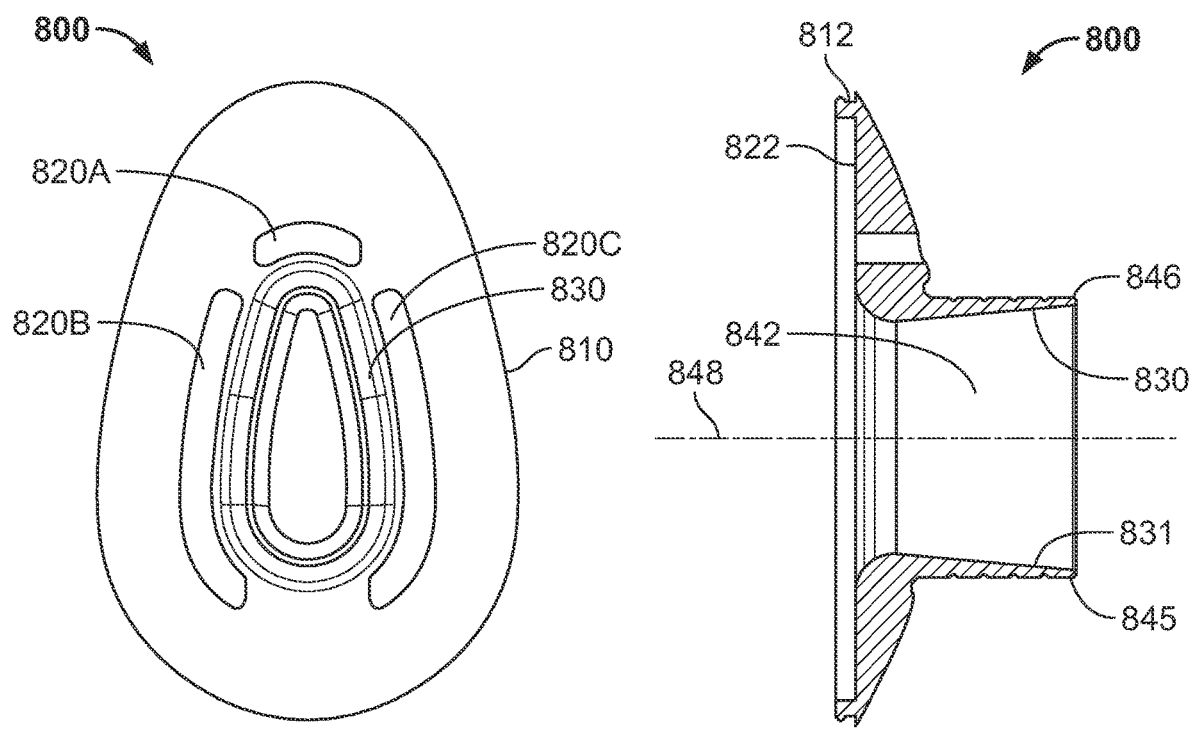
FIG. 20
FIG. 21

ANATOMIC IMPLANT FOR JOINTS

CROSS-REFERENCE TO RELATED APPLICATION

This application claims the benefit of the filing date of U.S. Provisional Patent Application No. 63/048,271 filed Jul. 6, 2020, the disclosure of which is hereby incorporated by reference herein in its entirety.

BACKGROUND OF THE DISCLOSURE

A damaged or diseased shoulder that requires treatment may be determined to require replacement. In such circumstances, known procedures such as total shoulder arthroplasty ("TSA") and reverse shoulder arthroplasty ("RSA") may be employed to carry out the replacement. These procedures may involve the placement of an implant in the glenoid, the humerus, or both.

A relevant part of such procedures is obtaining sufficient securement between the glenoid implant and the glenoid. Doing so not only ensures that the implant is properly positioned, but also increases the likelihood that the implant will last for a longer period of time. This is an ongoing challenge not only for implants in the shoulder, but also for implants in joints more generally. Further, the characteristics of an optimal articular surface of the implant may vary widely among patients. Thus, problems may arise if an articular surface part of a glenoid implant cannot be dimensioned in an optimal manner for a particular patient.

Thus, a need exists for glenoid implants with greater versatility, load bearing capacity and longevity once implanted in a patient.

BRIEF SUMMARY OF THE DISCLOSURE

The present disclosure addresses challenges extant with glenoid implants by providing an implant with an anatomically shaped keel for improved securement with bone and improved methods of securing such implants. These methods may also be advantageous when employed in other joints of the body. Additionally, the present disclosure contemplates an articular surface part of a glenoid implant with a bump on a non-exposed surface opposite the articular surface to allow for a greater range in the depth and radius of the articular surface. This may be accomplished by having a bottom side that protrudes away from the articular surface to allow such articular surface to extend deeper into a central region of the implant.

In one aspect, the present disclosure relates to a glenoid implant. In one embodiment, a first glenoid implant may include a body with an articulation surface, a bone facing surface and a keel. The keel may have a depth extending from the bone facing surface to a free end of the keel remote from the bone facing surface. Further, the keel may have a first width and a first thickness both measured in a plane perpendicular to a direction of the depth. The first width may be perpendicular to the first thickness and may extend from an inferior end of the keel to a superior end of the keel. The first thickness may taper from a first location along the first width adjacent to the inferior end toward the superior end.

In some embodiments of the first glenoid implant, the body may have a second width and a second thickness. The second width may be perpendicular to the second thickness and may extend from an inferior end of the body to a superior end of the body. The second thickness may taper from a second location along the second width adjacent to the inferior end of the body toward the superior end of the body. In other embodiments, the first width may have a first width portion and a second width portion. The first width portion may extend from the inferior end of the keel to a first location and the second width portion may extend from the first location to the superior end of the keel. The second width portion may be at least two times longer in a superior-inferior direction than the first width portion. In further examples, the second width portion may be at least three times longer in the superior-inferior direction than the first width portion.

In some embodiments of the first glenoid implant, the keel may be hollow and defined by an enclosed wall, the enclosed wall having a superior part, an inferior part, a first side part and a second side part. The superior part may have a first radius of curvature and the inferior part may have a second radius of curvature greater than the first radius of curvature. In other embodiments, the keel may have an ovoid shape in a cross-section cut at a first distance from the free end of the keel, the ovoid shape being symmetric about a single axis. In some embodiments, the keel may have a polygonal shape in a cross-section cut at a first distance from the free end of the keel. In some embodiments, the keel may be hollow and include three separate openings. In some embodiments, the three separate openings may include a first opening, a second opening and a third opening, the first opening at the free end of the keel, and the second and third openings being opposite one another on side surfaces of the keel in between the bone facing surface of the body and the free end. In some embodiments, the keel may include an outward facing protrusion around its perimeter at the free end. In some embodiments, the body may include a first peg and a second peg, each of the first and second pegs extending from the bone facing surface of the body. In some embodiments, the body may include a plurality of slots therethrough, each of the slots having an edge portion parallel to an outer surface of the keel. In some embodiments, the keel may have an outer surface with a plurality of notches thereon, each of the plurality of notches having a length that extends around a perimeter of the keel and being oriented perpendicular to the direction of the depth of the keel. In some embodiments, the keel may have an outer surface with a plurality of protrusions thereon. Each the plurality of protrusions may have a length that extends around a perimeter of the keel and have an orientation perpendicular to the direction of the depth of the keel. In some embodiments, the keel may include a plurality of slits parallel to the direction of the depth of the keel. The slits may be sized and spaced to increase a flexural capacity of the keel. In some embodiments, the body may include a metallic medial part and a polymeric lateral part.

In one embodiment, a second glenoid implant includes a body and a keel. The body includes an articulation surface and a bone facing surface. The keel has a depth extending from the bone facing surface to a free end of the keel remote from the bone facing surface. The keel has a first length and a first width both measured in a plane perpendicular to a direction of the depth, the first width being perpendicular to the first length. The first length may be defined by a first distance from an inferior end of the keel to a superior end of the keel. The first width may be measured at a first location adjacent to the inferior end. The keel may have a width dimension along a first portion of the keel from the first location to the superior end that tapers from the first location toward the superior end.

In some embodiments of the second glenoid implant, the width dimension along the first portion of the keel decreases in a linear manner over at least part of a distance between the first location and the superior end of the keel. In other embodiments, the keel may have a second portion that extends from the inferior end of the keel to the first location, and the first portion of the keel may be at least two times longer in a superior-inferior direction than the second portion. In other embodiments, the first portion of the keel may be at least three times longer in the superior-inferior direction than the second portion. In still further embodiments, the keel may be hollow and defined by an enclosed wall. The enclosed wall may have a superior part, an inferior part, a first side part and a second side part. The superior part may have a first radius of curvature and the inferior part may have a second radius of curvature greater than the first radius of curvature. In some embodiments, the keel may have an ovoid shape in a cross-section cut at a third distance from the free end of the keel, the ovoid shape being symmetric about a single plane. In some embodiments, the keel may have a polygonal shape in a cross-section cut at a first distance from the free end of the keel. In still further embodiments, the keel may be hollow and include three separate openings. In some embodiments, the keel may be hollow and include a first opening, a second opening and a third opening. The first opening may be located at the free end of the keel, and the second and third openings may be located opposite one another on side surfaces of the keel in between the bone facing surface of the body and the free end.

In some embodiments of the second glenoid implant, the keel may include an outward facing protrusion around its perimeter at the free end. In other embodiments, the body may include a first peg and a second peg, each of the first and second pegs extending from the bone facing surface of the body. In some embodiments, the body may include a plurality of slots therethrough, each of the slots having an edge portion parallel to an outer surface of the keel. In other embodiments, the keel may have an outer surface with a plurality of notches or protrusions thereon. Each of the plurality of notches or protrusions may have a length that extends around a perimeter of the keel and may be oriented perpendicular to the direction of the depth of the keel. In still further embodiments, the keel may include a plurality of slots parallel to the direction of the depth of the keel. The inclusion of the plurality of slots may increase deformability of the keel relative to a keel that is absent any slits. In some embodiments, the keel may have an outer surface with a plurality of protrusions thereon. Each of the plurality of protrusions may have a length that extends around a perimeter of the keel and have an orientation perpendicular to the direction of the depth of the keel.

In some embodiments of the second glenoid implant, the body may include a metallic medial part and a polymeric lateral part. In other embodiments, a second length of the body of the glenoid implant may be defined by a second distance from an inferior end of the body to a superior end of the body. The body may have a second width measured at a second location adjacent the inferior end of the body, the second width being perpendicular to the second length. The body may have a width dimension along a second portion of the body from the second location to the superior end of the body that tapers from the second location toward the superior end of the body.

In one embodiment, a third glenoid implant may include a medial part with a bone facing surface and a lateral part. The lateral part may include a lateral facing surface with a concave portion and a medial facing surface configured to couple to the medial part. The medial facing surface may include a peripheral region and a central region, the peripheral region separating an outer edge of the lateral part from the central region, and the central region having a protrusion relative to the peripheral region. The peripheral region may abut the central region along the inner edge. And, the lateral part may have a first thickness at the outer edge, a second thickness at the inner edge, and a third thickness in the central region, the second thickness being less than the first thickness and the third thickness being no less than the second thickness.

In some embodiments of the third glenoid implant, the third thickness may equal the second thickness. In other embodiments, the second thickness may be at least 3 mm. In some examples of these embodiments, the second thickness may be in a range from 3 mm to 5 mm. In still further embodiments, the medial facing surface of the lateral part may have a first surface area coincident with the peripheral region and a second surface area coincident with the central region, the first surface area being up to 200% larger than the second surface area. In some embodiments, the medial facing surface of the lateral part may have a first surface area coincident with the peripheral region and a second surface area coincident with the central region, the second surface area being larger than the first surface area. In some embodiments, the protrusion may have a convex surface. In some embodiments, the convex surface of the protrusion may have a radius in a range from 15 mm to 30 mm. In some embodiments, the protrusion may include a planar surface. In some embodiments, the inner edge may be a circle. In some embodiments, the concave portion of the lateral facing surface of the lateral part may have a radius in a range from 15 mm to 30 mm. In some embodiments, the radius of the concave portion of the lateral facing surface of the lateral part is in a range from 22 mm to 24 mm. In some embodiments, the medial part may include a keel that extends from the bone facing surface. The keel may include a first opening with a rotatable blade disposed therein. The blade may be rotatable from a first position to a second position. The blade may be positionable so that an entirely of the blade is within the keel in the first position and at least part of the blade is outside of the keel in the second position.

In one embodiment, a fourth glenoid implant includes a body and a keel. The body includes a medial facing surface and a lateral facing surface, and the keel extends from the medial facing surface of the body. The keel may include a first opening with a rotatable blade disposed therein. The rotatable blade may be movable between a first position and a second position within the opening. When in the first position, the blade may be entirely within the keel. When in the second position, the blade may be at least partially outside of the keel. In some examples, the blade may be rotatable about an axis through the keel and aligned along a depth of the keel. In some examples of these embodiments, the blade may be centered on the axis of rotation. In some examples of the fourth glenoid implant, the blade may have a boomerang-type shape. In some embodiments, the blade may be actuated by a mechanism attached to the glenoid implant. In some examples, the mechanism is a screw. In some of these and other examples, the screw is attached to the body. In some embodiments, the keel may further include a second opening with a second blade such that the second opening is at a different distance from the body than the first opening. In some examples of these embodiments, the second blade and the first blade may be independently rotatable or otherwise independently actuatable.

In some embodiments, the first glenoid implant may include one or more features from one or more of the second, third and fourth glenoid implants. In some embodiments, the second glenoid implant may include one or more features from one or more of the first, third and fourth glenoid implants. In some embodiments, the third glenoid implant may include one or more features from one or more of the first, second and fourth glenoid implants. In some embodiments, the fourth glenoid implant may include one or more features from one or more of the first, second and third glenoid implants.

In another aspect, the present disclosure relates to a method of implantation of a glenoid implant. In one embodiment, the method may include: resecting a glenoid to remove a closed loop groove of bone material without disturbing a bone portion interior to the closed loop groove; and inserting the glenoid implant into the glenoid, a keel of the glenoid implant being received in the closed loop groove such that the bone portion is disposed within a hollow interior of the keel, the keel engaging with an internal surface within the glenoid, the internal surface defining part of the closed loop groove.

In some embodiments, resecting the glenoid to remove the closed loop groove of bone material may involve removing a pear shaped path of bone material in the glenoid. In some embodiments, resecting the glenoid to remove the closed loop groove of bone material may involve removal of bone material such that a width of the closed loop groove is smaller further from an outer surface of the glenoid. In some embodiments, when the glenoid implant is inserted into the glenoid, the keel may bend such that a surface of the keel applies pressure onto the internal surface. In some embodiments, the resecting step may be performed by an end effector of a robot. In some embodiments, no bone substitute materials are disposed into the keel or the closed loop groove in the performance of the method. In some embodiments, the method may include a step of disposing bone substitute materials into the keel or the closed loop groove. In some embodiments, the method may include a step of resecting an undercut in an outward direction from a maximum depth of the closed loop groove.

BRIEF DESCRIPTION OF THE DRAWINGS

The present disclosure will be better understood on reading the following detailed description of non-limiting embodiments thereof, and on examining the accompanying drawings, in which:

FIGS. 13 and 14 are perspective and side views, respectively, of a glenoid implant according to another embodiment of the present disclosure;

FIGS. 19, 20 and 21 are perspective, lateral facing and sectional views, respectively, of a glenoid implant according to another embodiment of the present disclosure;

DETAILED DESCRIPTION

As used herein, the term "medial" when used in reference to a prosthetic implant refers to a position closer to the mid-line of the patient's body when the prosthetic implant is implanted in an intended position and orientation, whereas the term "lateral" means farther away from the mid-line of the patient's body. As used herein, the term "superior" when used in reference to a prosthetic implant refers to a position closer to the top or head of the patient's body when the prosthetic implant is implanted in an intended position and orientation, whereas the term "inferior" means closer to the bottom or feet of the patient's body. As used herein, the term "anterior" when used in reference to a prosthetic implant refers to a position closer to the front of the patient's body when the prosthetic implant is implanted in an intended position and orientation, whereas the term "posterior" means closer to the rear of the patient's body.

The present disclosure is directed to mammalian joint implants and methods related to same, including methods of bone preparation and methods of implant placement. Although many embodiments of the disclosure are directed to shoulder implants, it should be appreciated that the features of the implants and their methods of use are contemplated for other joints in a mammalian body, such as other ball-and-socket joints including the hip, as well as other non-ball-and-socket joints including the knee and the ankle.

Figure 1:
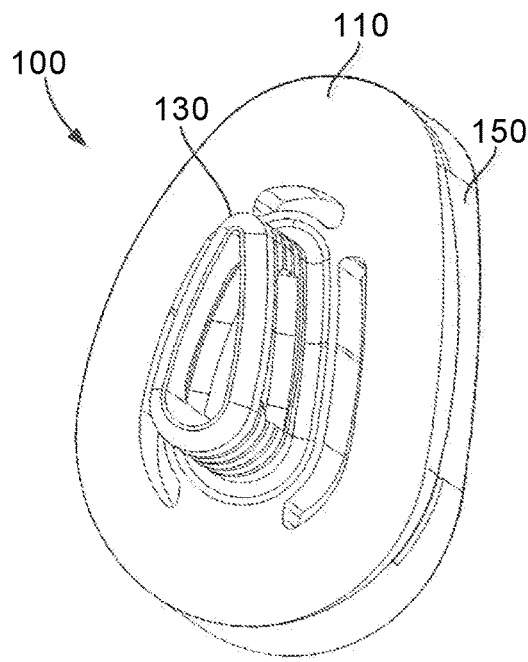
FIG. 1 is a perspective view of a glenoid implant according to one embodiment of the present disclosure.
Figure 2:
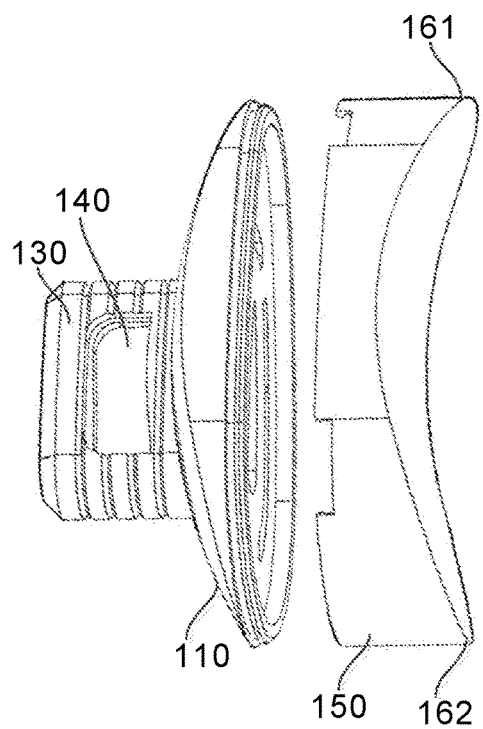
FIG. 2 is an exploded view of the glenoid implant of FIG. 1.
Figure 3:
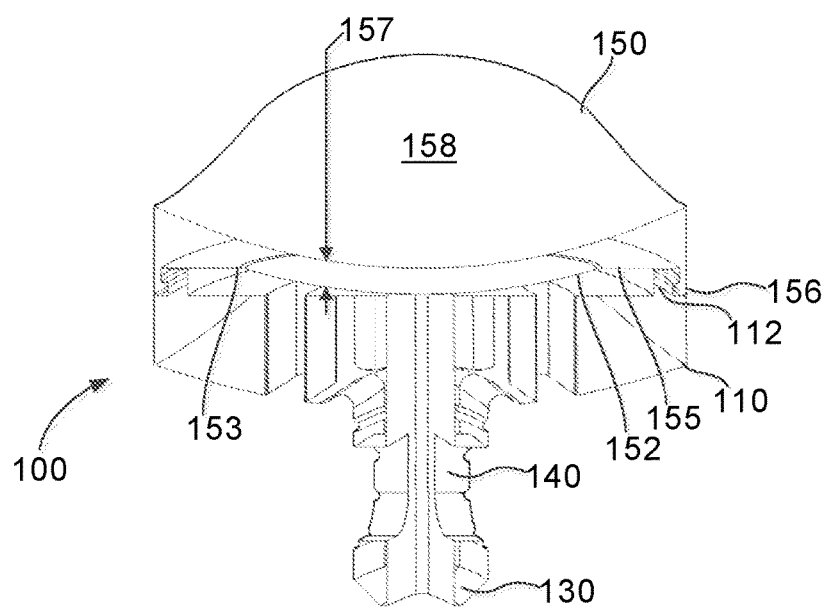
FIG. 3 is a cross-section of the glenoid implant of FIG. 1.

In a first aspect, the present disclosure relates to a glenoid implant. One embodiment of the glenoid implant and its constituent parts is shown in FIGS. 1-7. In this embodiment, the glenoid implant is designed for TSA, although it should be appreciated that the concepts described herein may be applied in either TSA or RSA. Similarly, other embodiments of the present disclosure that are explicitly directed to RSA may be modified for use in TSA procedures and vice versa. Glenoid implant 100, as shown in FIGS. 1-3, includes a medial part 110 and a lateral part 150. Medial part 110 is the anchor component of the implant for placement into the glenoid, while the lateral part includes an articulating surface that interfaces with the humerus. As shown in FIG. 3, medial part 110 includes an engagement feature 112 that interfaces with a complementary engagement feature 156 of the lateral part 150. The lateral part 150 is preferably polymeric and has capacity for flexure so that engagement feature 156 may flex or be bent around the corresponding engagement feature 112 on medial part 110 to snap fit the parts with one another. However, it should be understood that materials other than polymers may be suitable, particularly those that provide a suitable level of flexibility. Specific examples of material usable for lateral part 150 includes polycarbonate urethane and silicone rubber, both of which are biocompatible. Any imposed deformation of the lateral part 150 is elastic such that the snapping action results in the return of the lateral part to its original shape. In some arrangements, the fit between the lateral part 150 and medial part (110) may be a press fit, although other types of fit may be suitable. Each engagement feature 112, 156 may be a dovetail connection, as shown, though other types of engagement features are also contemplated.

Figure 4:
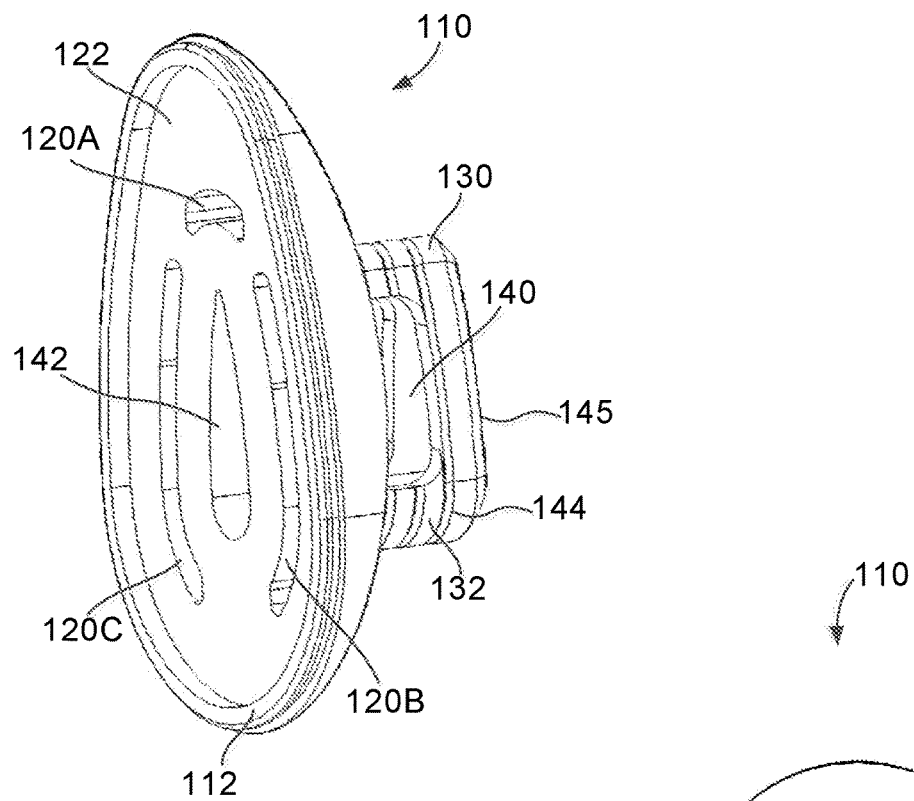
FIG. 4 is a perspective view of a medial part of the glenoid implant of FIG. 1.
Figure 5:
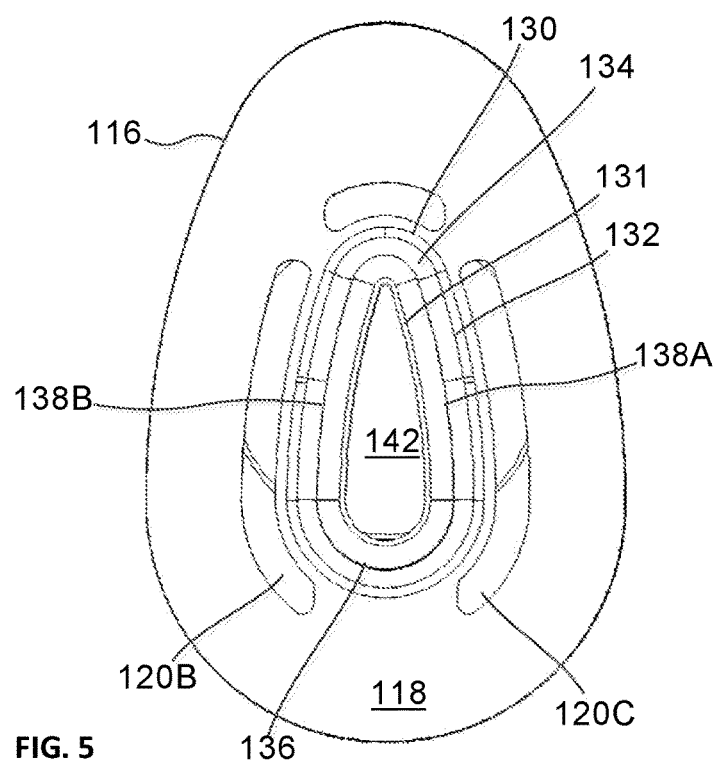
FIG. 5 is a lateral facing view of the medial part of FIG. 4.

FIGS. 4-5 show the medial part 110 in isolation. Medial part 110 includes a medial surface 118 that is generally convex in shape, and has a keel 130 extending medially therefrom. An outer layer of medial part 110 including medial surface 118 preferably has a porous structure that facilitates bone ingrowth. On an opposite side of medial part 110 is a lateral surface 122, shown in FIG. 4. Lateral surface 122 is generally planar and includes engagement feature 112 around its perimeter. Extending through lateral surface 112 are three separate slots 120A-C that surround a central opening 142. Central opening 142 has a tear drop shape and extends through medial part 110. In some arrangements, central opening 142 may extend through an entire length of keel 130. In other embodiments, central opening 142 may have a pear shape. Slot 120A is shorter than slots 120B, 120C and is located superior to opening 142. Each slot 120B, 120C is positioned on an opposite side of the central opening 142 and extends approximately parallel to lateral sides of opening 142. All three slots 120A-C may have slightly curved edges along their lengths to generally follow a shape of keel 130 and opening 142, as best shown in FIG. 5. Inclusion of the slots 120A-C may provide access to the bone, for example via a bone-cutting tool, when the implant is in place to simplify a revision procedure. In other words, instead of cutting around the exterior perimeter of medial part 110 to remove the medial part from the bone, the bone may be cut through slots 120A-C to allow keel 130 to be removed from the bone, sparing a relatively large amount of bone.

An overall perimeter of medial part 110 is pear-shaped, as best shown in FIG. 5, the shape being generally similar to an outer edge of the glenoid surface. In other embodiments, the overall perimeter of medial part 110 may be tear-drop shaped. In particular, the illustrated pear shape is narrower toward a superior end and wider toward an inferior end. Outer dimensions of medial part 110 are guided by an outer dimension of the glenoid surface (glenoid fossa) itself. In particular, medial part 110 is designed to have a footprint similar to, but smaller than, a total surface area of the glenoid. In some examples, a first dimension of medial part 110 from a superior end to an inferior end may be from about 35.5 mm to about 42.5 mm. And, a second dimension from an anterior end to a posterior end, substantially orthogonal to the first dimension, may be from about 25.8 mm to 32.2 mm.

Keel 130 is hollow with central opening 142 passing therethrough, as mentioned above. Keel 130 may also include a graft window 140 as shown in FIGS. 1, 2 and 4 passing laterally therethrough. A shape of graft window 140 may be rectangular with one or more rounded corners as shown in FIG. 2, although it is contemplated that the shape may be square, obround, circular or other similar shapes. Along an outer surface 132 of keel 130 are grooves or notches 144 spaced apart from one another and oriented approximately parallel to lateral surface 122 in an inferior-superior alignment. The inclusion of notches 144 gives the keel 130 a larger surface area to increase contact with bone when implanted, which may provide better anchoring to the bone. The notches may have a U or V shaped profile. In some examples, the notches may be oriented orthogonally to the orientation of notches 144 shown in FIGS. 2 and 4. The structure of keel 130 itself may be anatomically shaped. That is, the keel 130 may have a shape that is consistent with that of the perimeter of medial part 110 as defined by outer edge 116. For medial part 110 as shown in FIGS. 1-5, keel 130 is pear shaped when viewed in a medial or lateral direction. Inclusion of a keel 130 with an anatomical shape, such as a pear shape, improves bone remodeling potential, e.g., renewal of bone tissue, post-implantation when compared to implants that include a keel with a non-anatomical shape. Keel 130 includes a superior part 134, an inferior part 136, and opposite side parts 138A-B that bridge a distance between the superior and inferior parts. The combined superior part 134, opposite side parts 138A-B and inferior part 136 define a continuous enclosed loop, as shown in FIG. 5. Keel 130 is wider nearer to inferior part 136 and has an inner surface 131 with a larger first radius of curvature at inferior part 136, measured about a medial-to-lateral axis through a length of the keel, than a second radius at superior part 134. Each side part 138A-B may have slight curvature so that inner surface 131 is concave in those parts, but the side parts have much less curvature than the respective end parts 134, 136. Side parts 138A-B become closer together moving toward superior part 134. A rim 145 at a terminal or free end of keel 130 may have a rounded edge, as shown in FIG. 1. However, as mentioned elsewhere in the disclosure, a profile of the rim may vary from that shown for implant 100.

Figure 6:
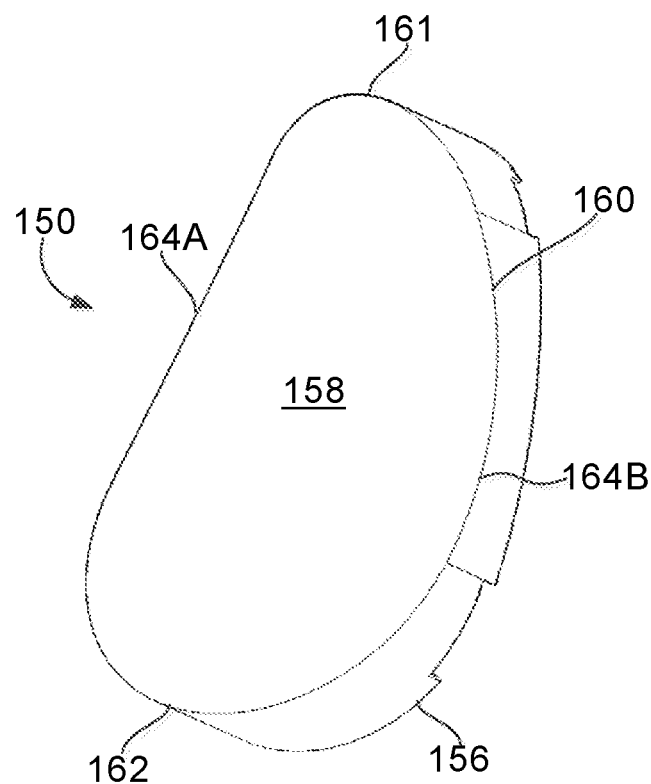
FIGS. 6 and 7 are both perspective views of a lateral part of the glenoid implant of FIG. 1.
Figure 7:
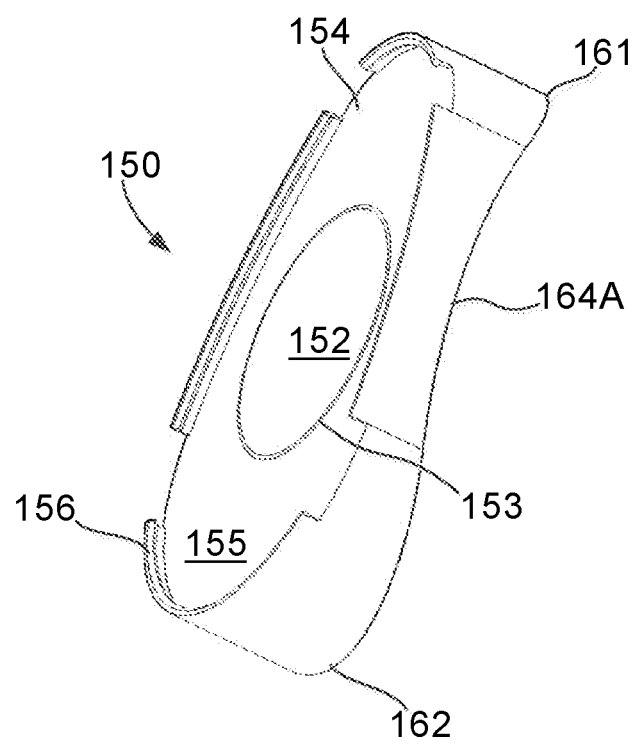

FIGS. 6-7 show lateral part 150 in isolation. Lateral part 150 includes articular surface 158 and medial surface 154 opposite the articular surface. Lateral part 150 has a varying depth (in the medial-to-lateral direction) along its length and width as a function of the concave shape of articular surface 158. A length of lateral part 150 extends from inferior apex 162 to superior apex 161. Articular surface 158 has a width (in the anterior-to-posterior direction) with a maximum closer to inferior apex 162 than superior apex 161. From a location with the maximum width, a width of the lateral part 150 tapers toward superior apex 161, as shown in FIG. 6. In this manner, from a front view, lateral part 150 has a pear-shape consistent with a shape of medial part 110. The shape of the articular surface 158 is bounded by edge 160. Further, because articular surface 158 is concave, the surface has low edge points 164A, 164B in between apices 161, 162. A radius of curvature of the concavity of articular surface 158 may be in a range from about 15 mm to about 30 mm. In some examples, the range may be from about 15 mm to about 25 mm. In further examples, the range may be from about 15 mm to about 23 mm. In further examples, the range may be from about 22 mm to about 24 mm. In yet another example, the radius of curvature may be about 23 mm. In other examples, the radius may be greater than about 30 mm.

Turning to the other side of lateral part 150, medial surface 154 has a central region 152 and a peripheral region 155 radially outward of the central region. An outer bound of peripheral region 155 includes a rim as shown in FIGS. 3 and 7, the rim including engagement feature 156. Central region 152 protrudes medially relative to peripheral region 155, as best shown in FIGS. 3 and 7. An outer extent of central region 152 interfaces with peripheral region 155 at edge 153, as shown in FIG. 7. As depicted, central region 152 includes a convex surface. In some alternative arrangements, the surface may be partially convex. In further arrangements, the surface of central region 152 may have planar parts. A size of the protrusion of central region 152 is preferably such that articular surface 158 extends to a depth at its lowest point that is close to a plane through peripheral region 155. This is best shown in FIG. 3. In some alternative arrangements, the central region 152 protrudes sufficiently relative to peripheral region 155 so that articular surface 158 crosses the plane through the peripheral region. Central region 152 provides extra material or structure to increase a minimum thickness of lateral part 150 in a portion of the lateral part that would otherwise be the thinnest part of the structure. Without the protruding surface of central region 152, a curvature of the articular surface 158 would be limited to one that would preserve a minimum thickness between an articular surface and a generally planar medial surface. With the protrusion of central region 152 included in lateral part 150, the lateral part may have a constant thickness 157 at or above a minimum threshold value at all locations of lateral part 150 within a perimeter of central region 152 defined by edge 153. A minimum threshold thickness value may be at least about 3 mm if lateral part 150 is formed of a polymer, such as polyethylene. Outside of edge 153, a thickness of lateral part 150 increases toward edge 160. This is shown, for example, in FIG. 3. Further to the depicted embodiment, at one extreme, a surface area of peripheral region 155 may be close to zero while a surface area of the central region 152 may occupy all or nearly all of the medial surface 154 of the lateral part 150. Conversely, a surface area of the central region 152 may be such that the surface area of peripheral region 155 is about 500% of the surface area of the central region. In this respect, the surface area of the central region 152 may be anywhere from about 15% to about 100% of a total surface area of the medial surface 154.

Implant 100 preferably utilizes a material combination such that medial part 110 is a metal material and lateral part 150 is a polymeric material. The metal may be a metal or metal alloy such as cobalt-chromium (CoCr) or Ti64. The polymeric material may be polyethylene such as X3 polyethylene by Stryker®. In some examples, the lateral part 150 may be ceramic or pyrolytic carbon instead of a polymer. It is contemplated that the aforementioned materials may be used in the respective medial and lateral parts of the glenoid implants of other embodiments of the present disclosure, including those illustrated in FIG. 8 through FIG. 22E, for example.

Figure 8:
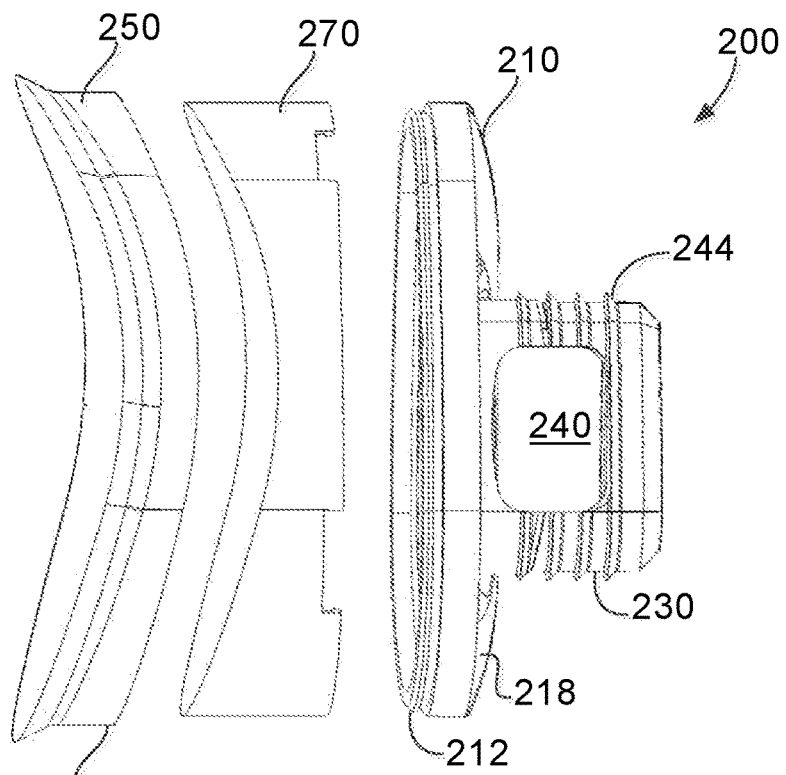
FIGS. 8 and 9 are exploded and section views, respectively, of a glenoid implant according to another embodiment of the present disclosure.
Figure 9:
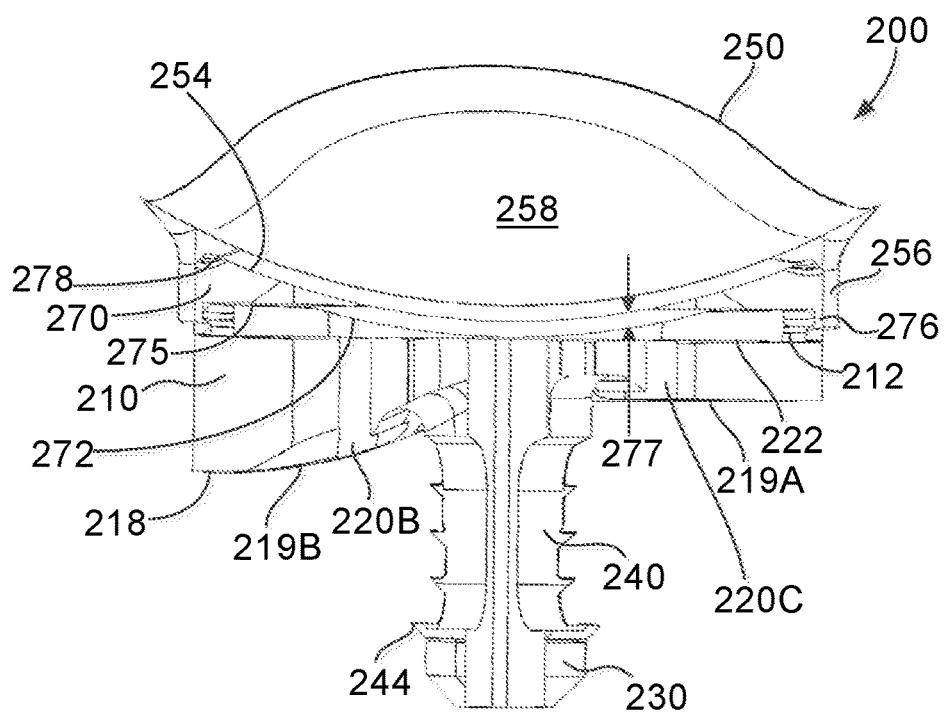

Another embodiment of a glenoid implant is shown in FIGS. 8 and 9. Unless otherwise stated, like reference numerals refer to like elements of implant 100, but within the 200-series of numerals. Glenoid implant 200 is an augmented implant and includes a medial part 210, a central part 270 and a lateral part 250. Medial part 210 is preferably metallic while central part 270 and lateral part 250 are preferably polymeric. In some examples, the material of the central part may be more rigid than the material of the lateral part. Lateral part 250 functions as a labrum part and may have flexural properties similar to that of rubber. Through the distinguishing characteristic of the central part, the central part may function as an insert to bridge the differences between the metallic material of the medial part and the flexible polymeric material of the lateral part. Medial part 210 includes engagement feature 212 on a periphery of lateral surface 222. Central part 270 includes engagement features 276 that are engageable with engagement feature 212. As shown in FIG. 9, the respective engagement features 212, 276 form a dovetail connection, though other connection types are contemplated, such as a snap fit connection. Lateral part 250, a flexible component, includes a peripheral wall 256 that forms a closed loop or ring sized so that when placed over central part 270, the lateral part engages with the central part through an interference fit. In some examples, a ring-shaped inward protrusion (not shown) on the peripheral wall of the lateral part engages with a ring-shaped groove on the central part, thereby establishing a compression fit.

Lateral part 250 includes an articular surface 258 and a medial surface 254, although unlike implant 100, medial surface 254 is a single convex surface throughout and does not have a protrusion or other distinctive sub-surface that deviates from the convex shape. Central part 270 may function as an insert between the medial part and the lateral part and includes a lateral surface 278 that is concave and sized and shaped such that when lateral part 250 is placed over and against lateral surface 278, as shown in FIG. 9, medial surface 254 of lateral part 250 and lateral surface 278 of central part 270 are flush with one another. Opposite the lateral surface of central part 270 is medial surface 272, 275. The medial surface of central part 270 includes a peripheral region 275 and a central region 272 that protrudes medially relative to peripheral region 275. The structure of the medial surface 272, 275 of central part 270 is similar to medial surface 154 of lateral part 150 in implant 100. Central region 272 as shown in FIG. 9 has a convex protrusion that is entirely surrounded by peripheral region 275. As with lateral part 150, central region 272 provides a thickness 277 of the lateral part at or above a set minimum, while also providing space so that lateral surface 278 has a deeper low point in a central area of the implant and a smaller radius of curvature than otherwise possible, if desired. In some examples, including that shown in FIG. 9, lateral surface 278 crosses a plane through peripheral region 275, a depth that, without the central protrusion, would result in a void in central part 270 toward its center.

Medial part 210 includes lateral surface 222 with engagement feature 212. As shown in FIG. 8, engagement feature 212 extends peripherally in a closed loop around an outer boundary of lateral surface 222. Opposite lateral surface 222 is medial surface 218. Medial surface 218 includes shallow portion 219A and wedged portion 219B. Wedged portion 219B extends along one side of keel 230 while shallow portion 219A extends along an opposite side, thereby roughly dividing medial surface 218 evenly between the two portions. Wedged portion 219B may be positioned on a posterior or an anterior side of the glenoid. For TSA applications, posterior-inferior wear tends to be very common, so in those circumstances, posterior positioning is typical. Wedged portion 219B protrudes relative to shallow portion as shown in FIG. 9 and has a slight convex contour. Surfaces of portions 219A-B are characteristic of augmented glenoid implant structures for use with patients having eccentric glenoid erosion, in which the wedged portion 219B is adapted to contact a neoglenoid surface and the shallow portion 219A is adapted to contact a paleoglenoid surface. Augmented glenoid surfaces, which may be used in place of those illustrated in FIGS. 8-9, are described in greater detail in U.S. Provisional Patent Application No. 62/873,266, filed Jul. 12, 2019, the disclosure of which is hereby incorporated by reference herein. Keel 230 of medial part 210 includes grooves, ribs or notches 244 which have extensions thereon, as shown in FIGS. 8 and 9. The extensions may have a "7"-shaped or "V"-shaped profile. Notches 244 with extensions function to compress bone upon impaction of implant 200 into bone. Although extensions on the notches 244 are not shown for implant 100, it is contemplated that such extensions may be included on the keel of any one of the implants of the present disclosure.

Figure 9A:
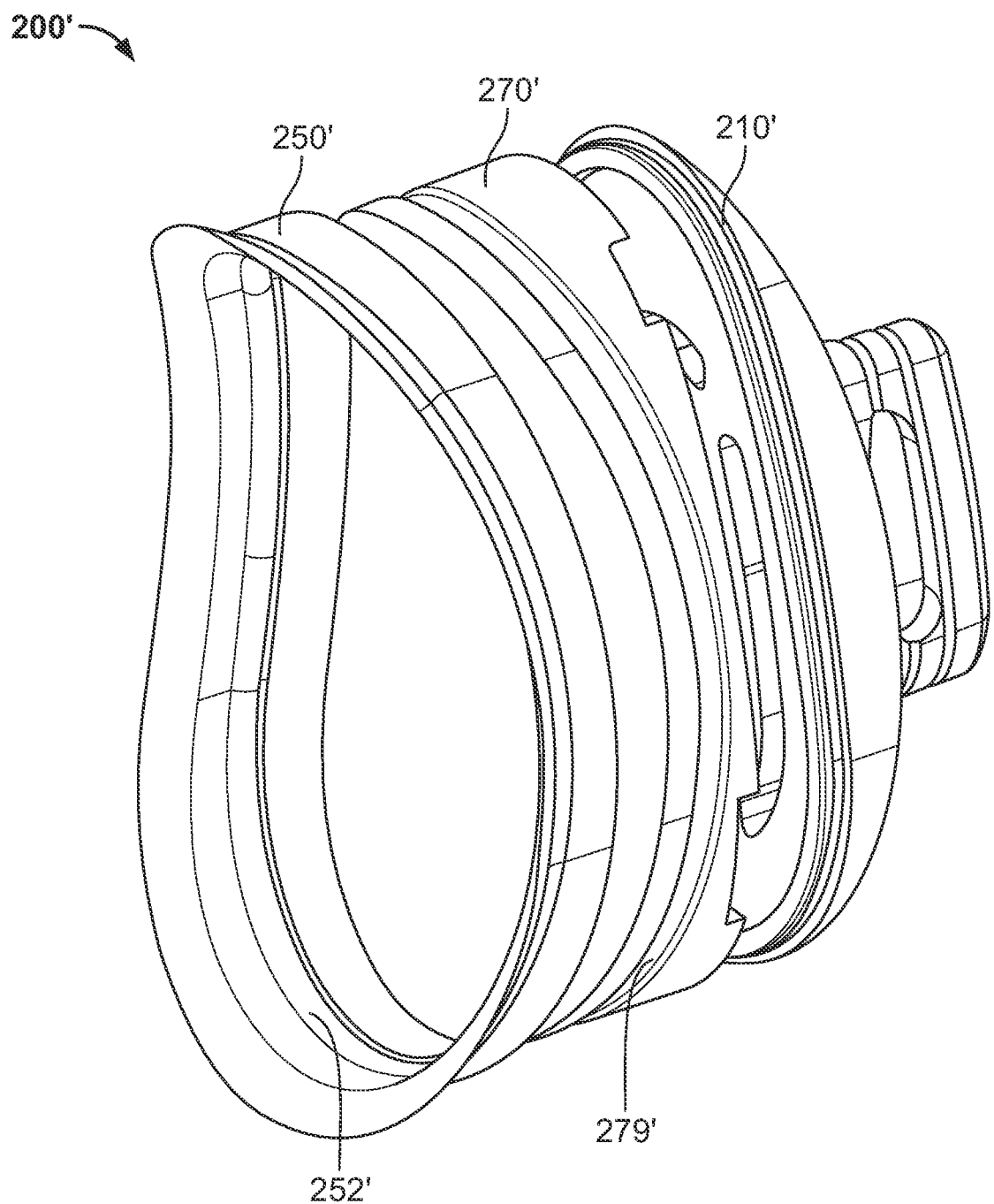
FIG. 9A is a perspective view of a glenoid implant according to another embodiment of the present disclosure.

In another embodiment, a complete glenoid implant may include medial part 210 and central part 270 alone, without the lateral part. With an implant assembled in such a manner, central part 270 functions as an articulation surface with the humeral implant head, e.g., an implant made of a metallic material such as cobalt-chromium (CoCr). In yet another embodiment, shown in FIG. 9A, a complete glenoid implant 200' may include medial part 210', central part 270', and a lateral part 250' in the form of a flexible ring, which has a length that extends around a perimeter of central part 270'. Lateral part 250' includes an inward facing protrusion 252' that is engageable with a complementary recess 279' on central part 270', the engagement being in the form of a compression fit. Lateral part 250' is hollow so that when implant 200' is fully assembled, an articular surface of central part 270' is exposed. In this manner, the articular surface of central part 270' is exposed to contact with a humeral implant post-surgery. In use, wear between the exposed surface of the glenoid implant 200' and the humeral head is minimized through the inclusion of lateral part 250'. Less wear results in less buildup of debris.

Figure 10:
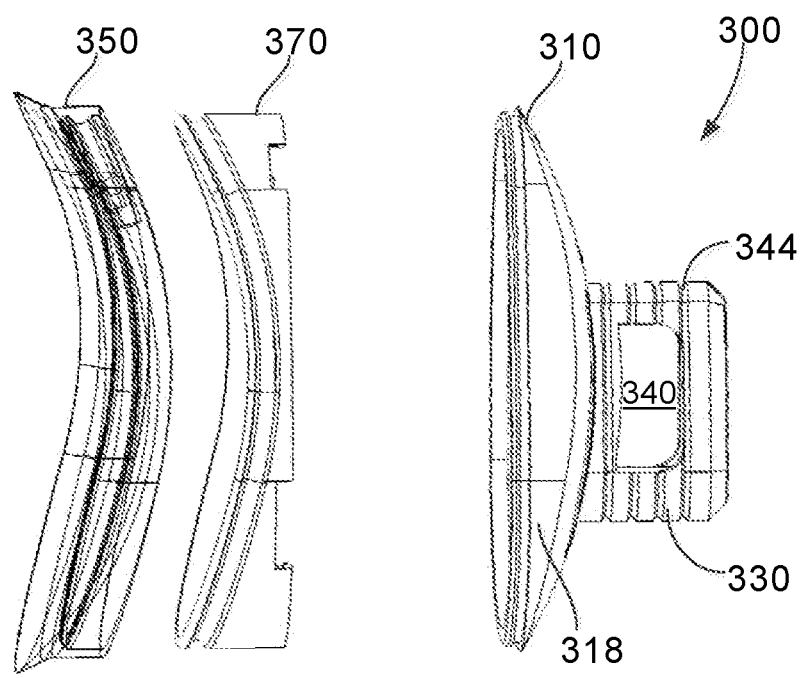
FIGS. 10 and 11 are exploded and section views, respectively, of a glenoid implant according to another embodiment of the present disclosure.
Figure 11:
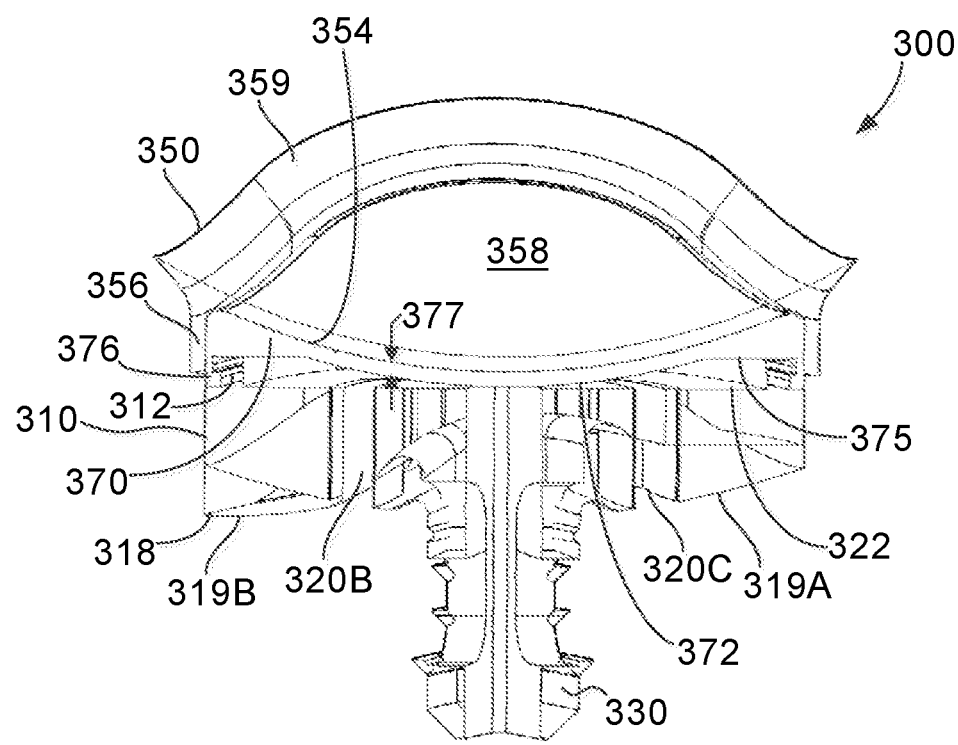

Glenoid implant 300 is yet another embodiment of the glenoid implant and is illustrated in FIGS. 10 and 11. Unless otherwise stated, like reference numerals refer to like elements of implants 100 and 200, but within the 300-series of numerals. Glenoid implant 300 includes many of the same features as implant 200, with distinctions as shown in the Figures and as described in the following. Glenoid implant 300 includes medial part 310, central part 370, and lateral part 350, each engageable with one another as shown in FIG. 11 and having engagement features that are the same as those described for glenoid implant 200. Lateral part 350 includes articular surface 358 with an outer part 359 curved as shown in FIGS. 10 and 11. Medial part 310 includes lateral surface 322 and medial surface 318. Medial surface 318 includes a first portion 319A and a second portion 319B, shown in FIG. 11. Second portion 319B tapers from an outer surface of medial part 310 toward keel 330 and first portion 319A tapers from the keel toward the outer surface. In this manner, medial part 310 is thicker in second portion 319B than in first portion 319A. As shown, medial surface 318 is generally convex, though the medial surface includes slots 320A-C therein. The shape of medial part 310 provides additional versatility for the glenoid implants contemplated by the present disclosure in that it may be used to accommodate different anatomy or surgical conditions than implants 100, 200, for example. This may be desirable if the labrum in the shoulder has a shape that is best accommodated by implant 300.

Figure 12:
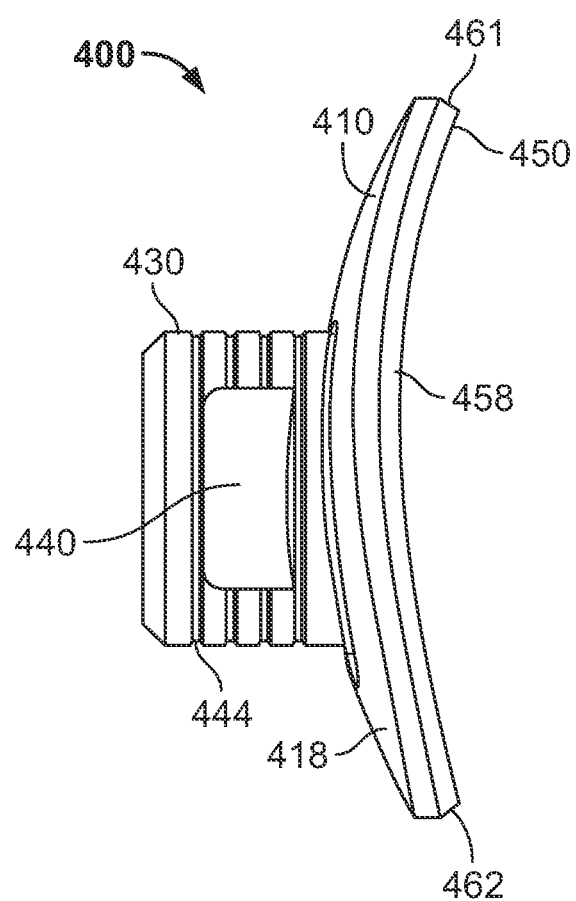
FIG. 12 is a side view of a glenoid implant according to another embodiment of the present disclosure.
Figure 12A:
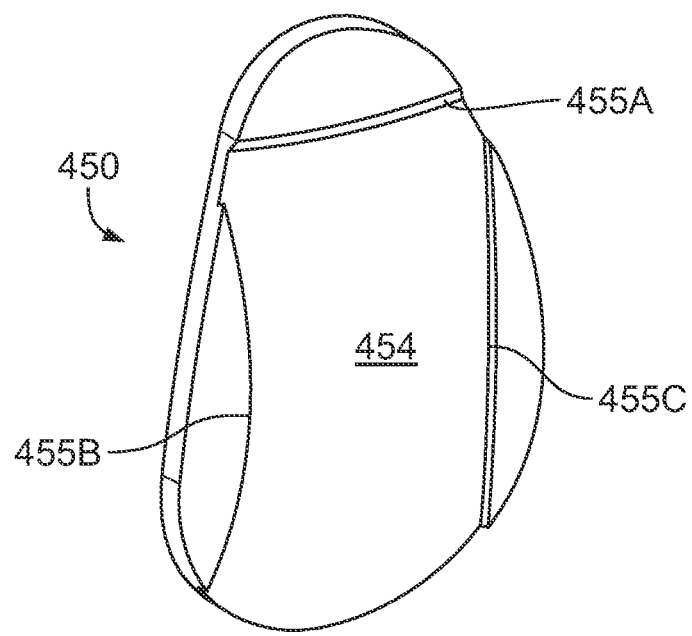
FIGS. 12A-B are perspective views of a lateral part and a medial part, respectively, of the glenoid implant of FIG. 12.
Figure 12B:
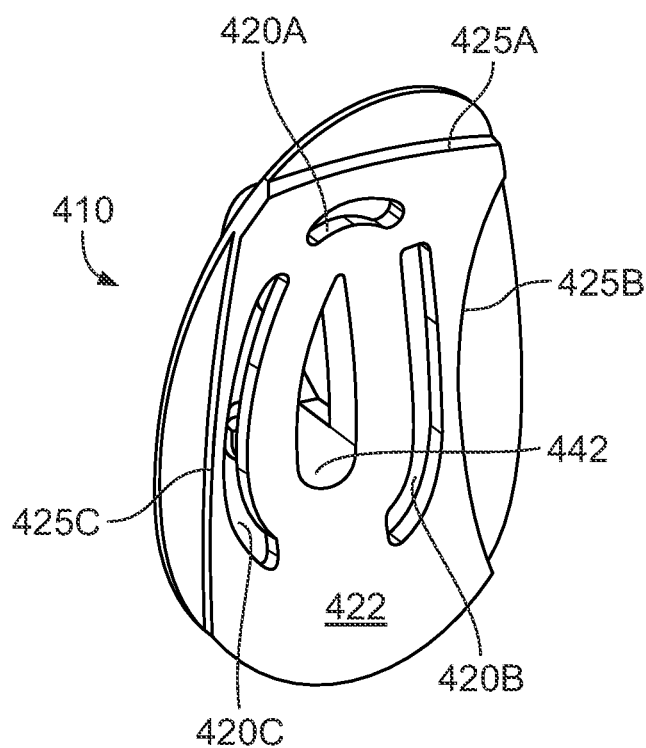

FIGS. 12, 12A and 12B illustrate yet another embodiment of the implant, glenoid implant 400. Unless otherwise stated, like reference numerals refer to like elements of implant 100, but within the 400-series of numerals. Implant 400 includes medial part 410 and lateral part 450. Medial part 410 includes a medial surface 418, a lateral surface 422 opposite the medial surface, and a keel 430 extending from the medial surface. Medial part 410 includes a central opening 442 through keel 430 and slots 420A-C. Medial surface 418 is convex in shape, with lateral surface 422 being generally parallel to the medial surface and thus having a concave shape. As shown in FIG. 12B, lateral surface 422 includes a superior ridge 425A and lateral ridges 425B-C, the ridges defining a protruding central region interior to the ridges. Lateral part 450 includes a medial surface 454 and an articular surface 458 opposite the medial surface. As shown in FIG. 12A, medial surface 454 includes a superior ridge 455A and lateral ridges 455B-C, the ridges defining a recessed surface interior to the ridges. Ridges 455A-C are complementary to ridges 425A-C. Through these respective surface features, lateral part 450 is engageable with medial part 410 by sliding lateral part 450 over medial part 410 from a position superior to the medial part and moving in an inferior direction until ridge 455A makes contact with ridge 425A. In implant 400, lateral part 450 has a generally uniform thickness throughout, so that a curvature of medial surface follows that of articular surface 458. The relatively thin structure of implant 400, as compared to implant 100, for example, improves the ability to place the implant into the glenoid through an inlay technique.

FIGS. 13 and 14 illustrate a glenoid implant 500 according to an embodiment of the disclosure. Unless otherwise stated, like reference numerals refer to like elements of implant 100, but within the 500-series of numerals. A medial part 510 of implant 500 is shown in FIGS. 13 and 14. On a medial surface 518 of the medial part 510, and centrally disposed, is keel 530. Also on medial surface 518 are pegs 524, 526, disposed on respective superior and inferior sides of the keel. As shown, medial part 510 has two pegs. Each peg has a cylindrical main body with a tapered tip. The tip as shown is partially spherical. In alternative arrangements, medial surface 518 may have any number of pegs. For example, medial surface 518 may have four, five or six pegs. The pegs may be arranged at equal spacing, in a pattern, or in another arrangement. In some arrangements, the pegs may have a different shape. For example, the pegs may include one or more planar surfaces and tips with shapes varying from that shown. Medial surface 518 may include surface characteristics for bone ingrowth, as is shown in FIG. 13.

Figures 15, 16:
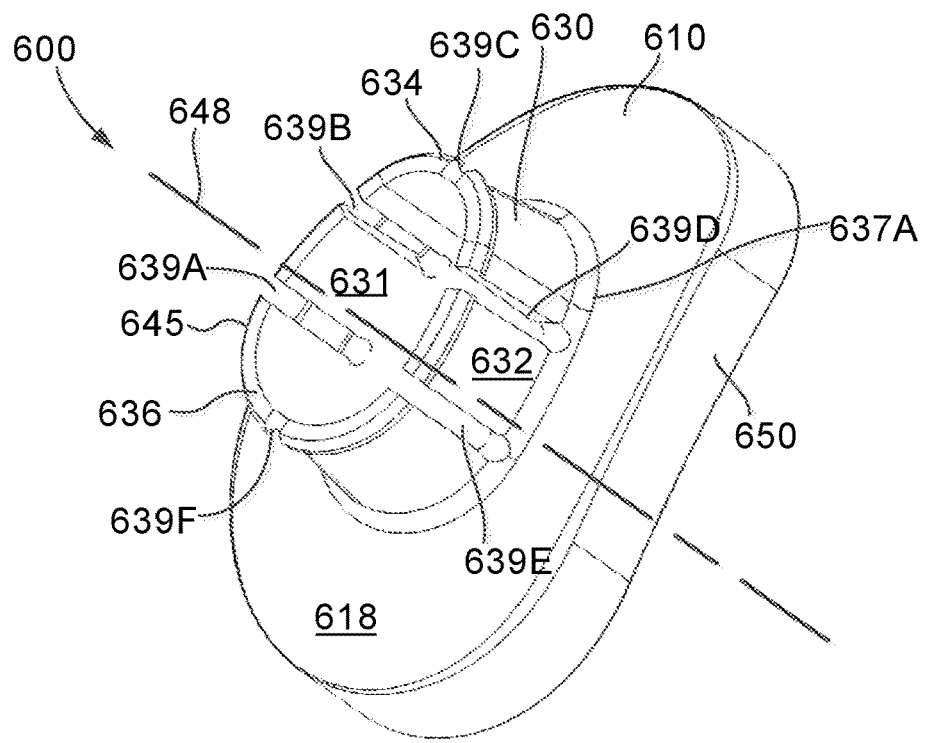
FIGS. 15 and 16 are perspective and sectional views, respectively, of a glenoid implant according to another embodiment of the present disclosure.

FIGS. 15 and 16 illustrate a glenoid implant 600 according to an embodiment of the disclosure. In FIG. 16, glenoid implant 600 is shown implanted into bone. Unless otherwise stated, like reference numerals refer to like elements of implant 100, but within the 600-series of numerals. Implant 600 includes medial part 610 and lateral part 650. Medial part 610 includes a keel 630 that extends from a central part of medial surface 618. Keel 630 is hollow and is pear-shaped when viewed along an axis 648 through the hollow part. Keel 630 is defined by a wall with an inner surface 631 and an outer surface 632. Keel 630 has a depth that extends from a base 637A-B of the keel to a lip 645 of the keel at the open end of the keel. Lip 645 extends around a length of the free end of keel 630 and includes an outward facing protrusion. From base 637A-B to lip 645, a thickness of the wall tapers as shown in FIG. 16. Punctuated at intervals along the wall around its peripheral dimension are slits 639A-F, six in total. As shown in FIG. 15, each slit extends from a first end at the lip to a second end adjacent to outer base 637A external to the wall or inner base 637B internal to the wall. At the second end, each slit 639A-F includes a bulge in size. The inclusion of the slits 639A-F and their position around the keel 630 render the keel flexible to an extent sufficient for implant installation into bone. In particular, the wall of keel 630 may bend toward or away from axis 648. In some arrangements, a greater or smaller number of slits may be included in the keel, and the shape of the slits may vary from that shown. Lateral part 650 is engageable with medial part 610 as described in other embodiments of the disclosure. Further, lateral part 650 includes a medial surface 654 with a protrusion 655 thereon. When assembled, protrusion 655 fits through a corresponding opening in inner base 637B of keel 630.

Figure 17:
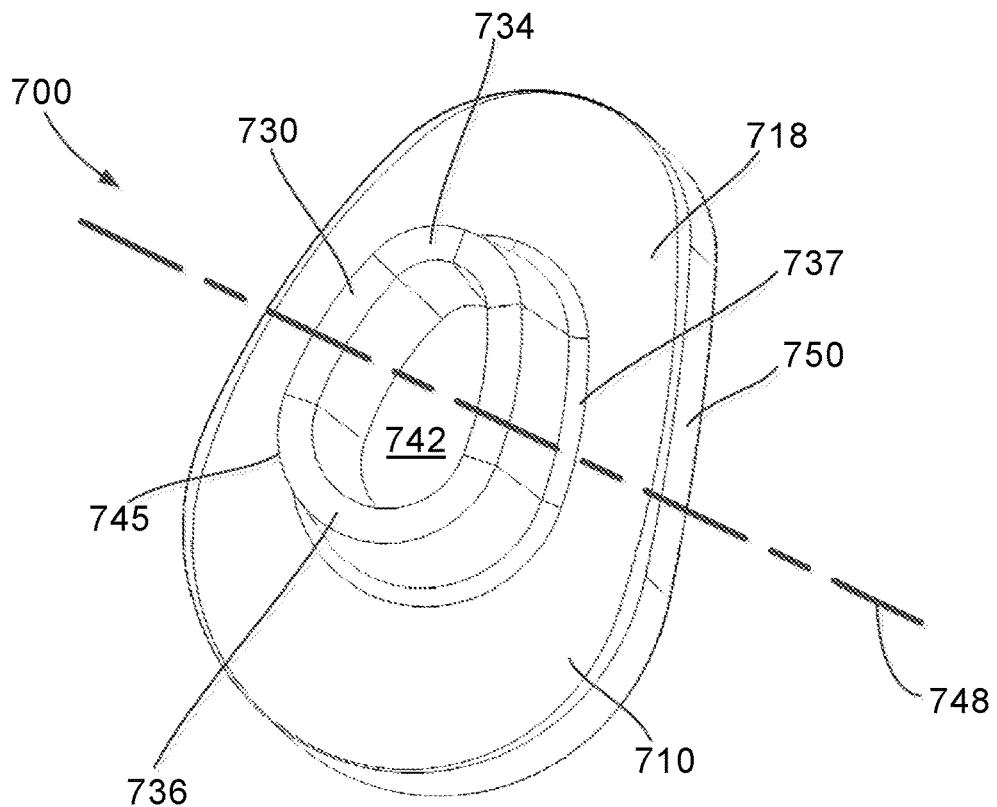
FIGS. 17 and 18 are perspective and sectional views, respectively, of a glenoid implant according to another embodiment of the present disclosure.
Figure 18:
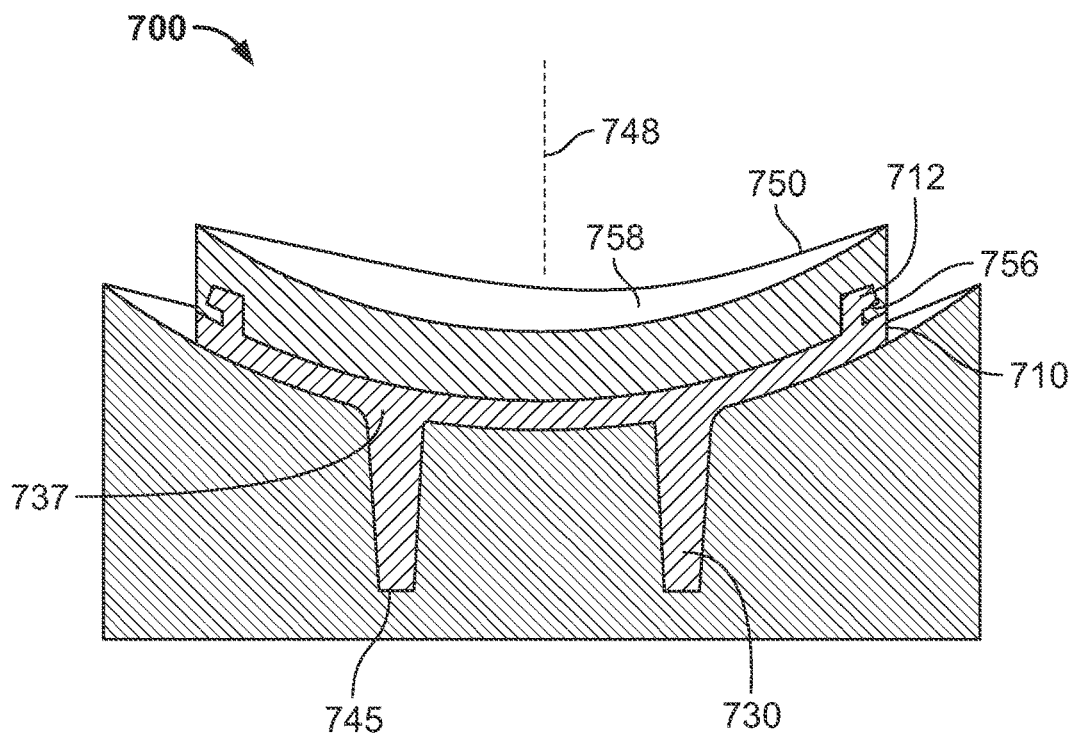

FIGS. 17 and 18 illustrate a glenoid implant 700 according to an embodiment of the disclosure. In FIG. 18, glenoid implant 700 is shown implanted into bone. Unless otherwise stated, like reference numerals refer to like elements of implants 100 and 600, but within the 700-series of numerals. Implant 700 includes medial part 710 and lateral part 750. A keel 730 extends medially from medial surface 718 of medial part 710. Keel 730 is hollow with an opening 742. The wall of keel 730 defines a pear-shape when viewed on axis 748 through a center of opening 742, and is solid throughout, as shown in FIG. 17. From a base 737 of the keel 730 to a rim 745 of the keel, the wall tapers, as shown in FIG. 18. Lateral part 750 is engageable with medial part 710 as described in other embodiments of the disclosure. In some arrangements, keel 730 may be a relatively solid metallic material while in other arrangements the keel maybe a relatively porous metallic material.

FIGS. 19-21 illustrate a glenoid implant 800 according to an embodiment of the disclosure. Unless otherwise stated, like reference numerals refer to like elements of implant 100, but within the 800-series of numerals. Implant 800 includes a medial part 810 and a lateral part (not shown) that attaches to a lateral surface 822 of medial part 810. Medial part 810 includes hollow keel 830 within opening 842 therein. Keel 830 has a thin wall with notches 844 on an outside surface. Keel 830 is a hard metallic material with strength sufficient so that bone may be compacted within the keel as it is implanted. The outer surface of keel 830, over its depth from base 837 to rim 845, is parallel to an axis 848 through the opening, as shown in FIG. 21. Inner surface 831 of keel 830, however, tapers from base 837 to rim 845. In this manner, a thickness of a wall of keel 830 tapers from the base to the rim. The tapered profile of the keel wall improves compaction of bone when the implant is impacted and otherwise placed onto the glenoid. Between base 837 of the keel 830 and medial surface 818 of the medial part is a transition surface 817 that encloses keel 830. The transition surface is recessed relative to medial surface 818 and is included to simplify the manufacturing process. In some arrangements, if implant 800 is formed through an additive manufacturing technique, medial surface 818 may be formed to abut keel 830 without a recess surrounding the keel.

Figure 22A:
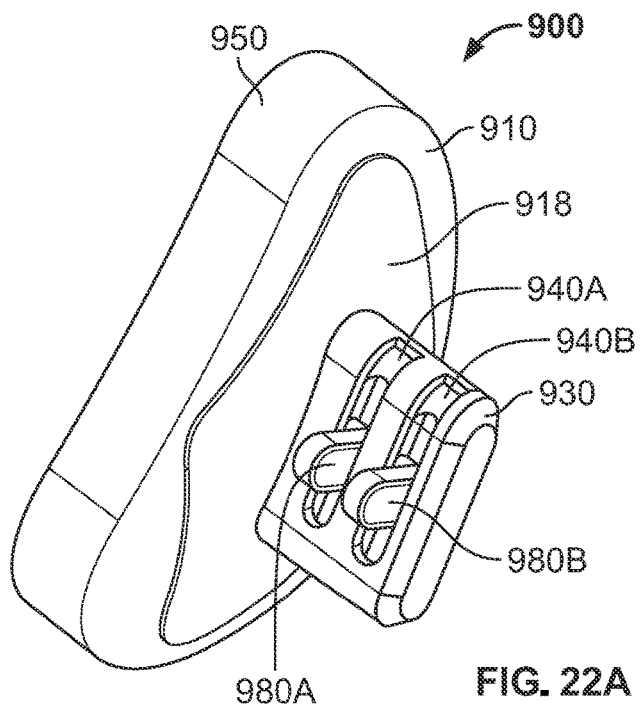
FIG. 22A is a perspective view of a glenoid implant according to another embodiment of the present disclosure.
Figure 22B:
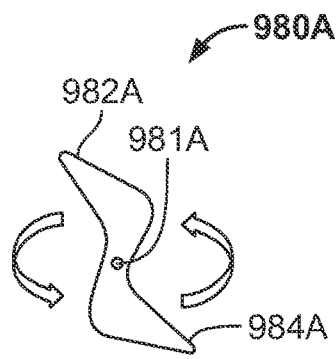
FIG. 22B is a close up view of a blade of the glenoid implant of FIG. 22A.
Figure 22C:
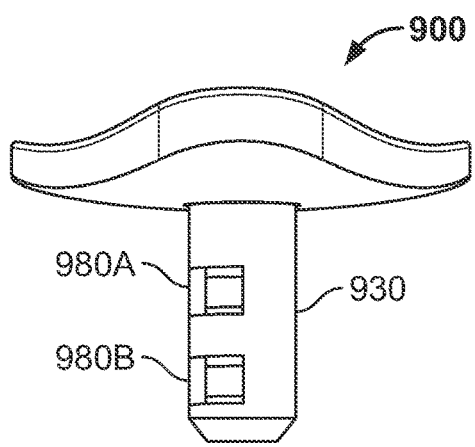
FIGS. 22C-D are front views of the glenoid implant of FIG. 22A.
Figure 22D:
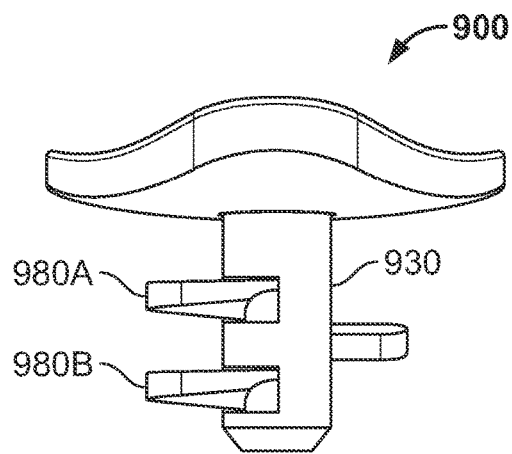
Figure 22E:
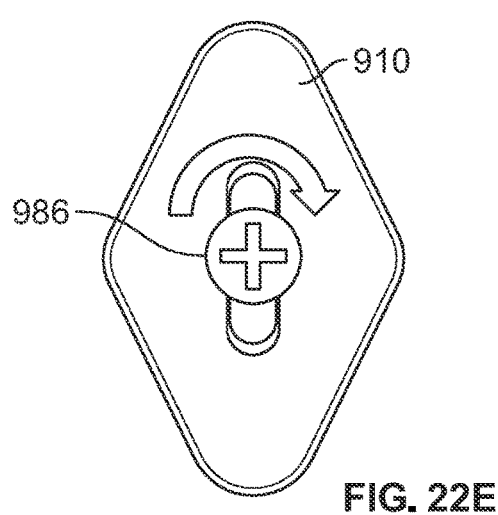
FIG. 22E is a partial view of the glenoid implant of FIG. 22A.

FIGS. 22A-E illustrate a glenoid implant 900 according to an embodiment of the disclosure. Unless otherwise stated, like reference numerals refer to like elements of implant 100, but within the 900-series of numerals. Implant 900 includes a medial part 910 and a lateral part 950. In some arrangements, medial part 910 may be porous titanium in a central region and a polymeric in a peripheral region. In one example of such arrangements, the titanium medial part is a base that is dipped in liquid polymer in a mold so that the polymer solidifies over the titanium medial part. Extending medially from medial surface 918 is keel 930, shown in FIG. 22A. Keel 930 has a generally rectangular sectional shape with rounded corners, and has such a shape throughout its depth. Keel 930 further includes openings 940A, 940B, separate from one another as shown in FIG. 22A. Each opening 940A-B has a length perpendicular to the depth of the keel 930. Disposed within opening 940A is a blade 980A and within opening 904B is a blade 980B. Each of these blades has a similar structure as shown in FIG. 22B where blade 980A is shown as representative. Blade 980A has a first end 982A and a second end 984A opposite first end 982A. On each side between the ends 982A, 984A is one concave bend and one convex bend such that the blade has a double sickle shape. A center of rotation of the blade 980A-B as it is positioned within the opening 940A-B of the keel 930 is indicated by reference numeral 981A. It is contemplated that a shape of these blades 980A-B may vary from that shown, provided that the shape allows for rotation within the openings 940A-B of the keel 930 as shown in FIGS. 22C-D. On a lateral side of medial part 910 is an opening with an actuation element disposed therein. In the depicted embodiment shown in FIG. 22E, the actuation element is a screw-type structure 986 that can be gripped by a driver element, such as a screw driver (not shown). Rotation of screw-type structure 986 causes blades to rotate about their centers 981 to control whether the blades are positioned mostly to entirely within keel 930 as shown in FIG. 22C or whether the blades project out of the keel as shown in FIG. 22D. It should be appreciated that blade 980B as depicted in FIGS. 22C-D includes a staggered shape such that implant 900 in FIG. 22D includes two blades in total. The application of this feature is described in greater detail below in the methods of use of the implant.

Figure 23:
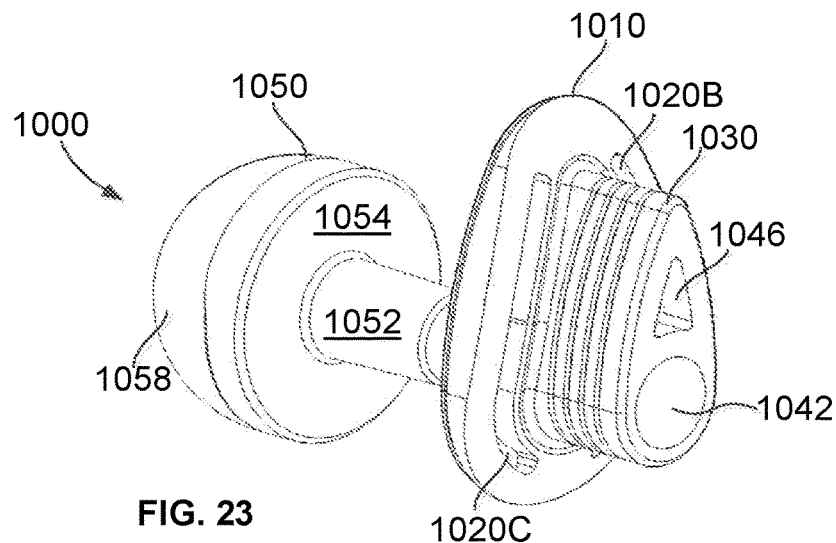
FIG. 23 is an exploded view of a glenoid implant according to another embodiment of the present disclosure.

FIG. 23 illustrates yet another embodiment of a glenoid implant, but for a reverse shoulder implanted for a RSA procedure. Glenoid implant 1000 includes a medial part 1010 and a glenosphere 1050 configured to be disposed in the medial part 1010. Preferably, the medial part 1010 and glenosphere 1050 are both formed of a metal or metal alloy. Medial part 1010 includes keel 1030. Keel 1030 includes two openings 1042, 1046 extending in parallel directions along a depth of the keel. Opening 1042 is round and forms a cylindrical path through the keel 1030 sized to receive an engagement portion 1052 of glenosphere 1050. Opening 1046 is triangular such that a path defined through the keel 1030 is a triangular prism and functions to receive bone graft or other bony ingrowth during implant use. Keel 1030 has an outer surface that is pear shaped and includes notches 1 thereon. Through medial part 1010 and on opposite sides of the keel 1030 are slots 1020B, 1020C. Glenosphere 1050 includes a hemispherical surface 1058 and a medial surface 1054 that presses onto or toward medial part 1010 when engaged thereto.

Figure 24:
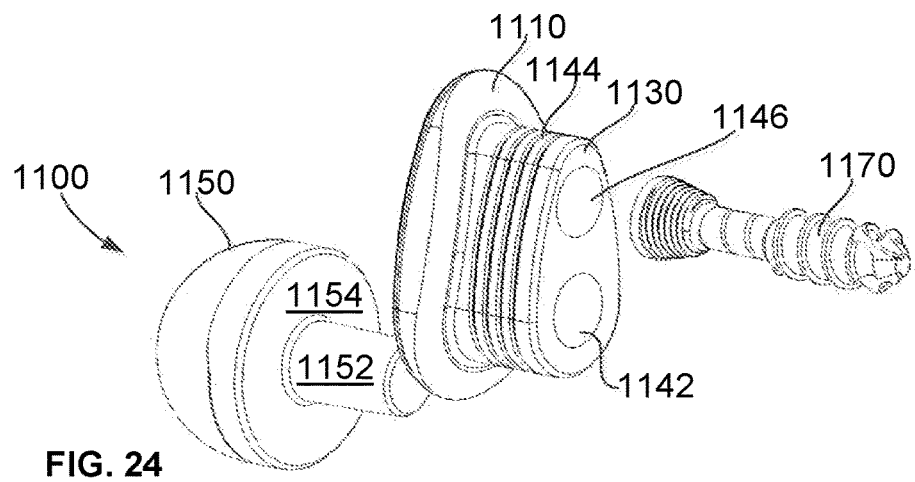
FIGS. 24 and 25 are exploded and sectional views, respectively, of a glenoid implant according to another embodiment of the present disclosure.
Figure 25:
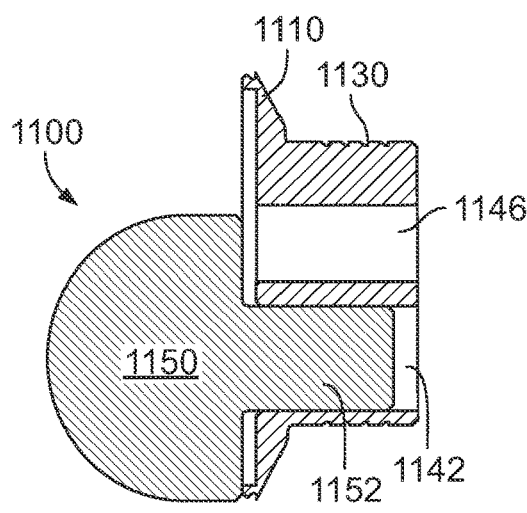

Glenoid implant 1100 illustrated in FIG. 24, another embodiment of the disclosure, is also for a RSA procedure. Unless otherwise stated, like reference numerals refer to like elements of implant 1000, but within the 1100-series of numerals. Both medial part 1110 and glenosphere 1150 are preferably metallic. In implant 1100, however, while keel 1130 has two parallel openings 1142, 1146, opening 1146 is cylindrical and sized to receive a fastener 1170. Fastener 1170 has surface characteristics for engagement with bone, in furtherance of the purpose of implant 1100. In medial part 1110, opening 1142 is defined by an inner wall that is tapered in toward a lateral surface of medial part. This is sometimes referred to as a Morse taper and is shown in FIG. 25. The inclusion of the Morse taper enhances engagement between engagement portion 1152 of glenosphere 1150 and medial part 1110.

Figure 26:
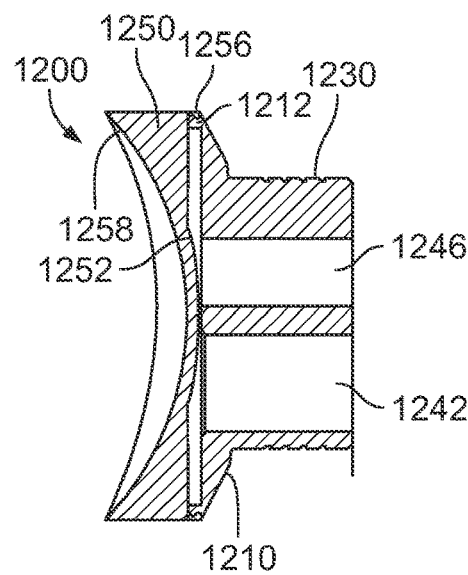
FIG. 26 is a sectional view of a glenoid implant according to another embodiment of the present disclosure.
Figure 27:
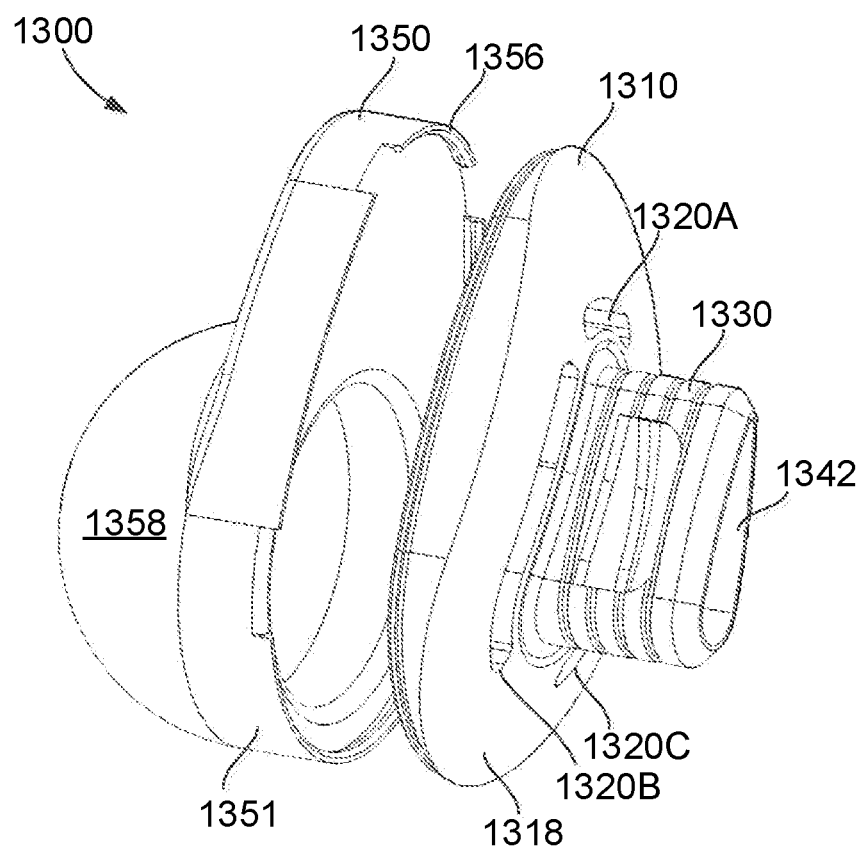
FIG. 27 is a perspective view of a glenoid implant according to another embodiment of the present disclosure.

FIG. 26 illustrates an embodiment of a glenoid implant 1200 that utilizes a metallic medial part 1210 that is the same as medial part 1110, but includes a polymeric lateral part 1250 attached thereto. This allows a lateral part with a concave articular surface to be substituted with a glenosphere such as that described for FIG. 25 and vice versa. Unless otherwise stated, like reference numerals refer to like elements of implants 100, 1100, but within the 1200-series of numerals. FIG. 27 illustrates an embodiment of a glenoid implant 1300 that includes medial part 1310 and lateral part 1350. Unless otherwise stated, like reference numerals refer to like elements of implants 100, 1000, but within the 1300-series of numerals. Medial part 1310 is preferably metallic and lateral part 1350 is preferably polymeric. Medial part 1310 includes a keel 1330 extending medially from medial surface 1318. Keel 1330 has a structure consistent with keel 130. Lateral part 1350 includes a glenosphere with a hemispherical surface 1358 at an inferior end on top of a base 1351. Base 1351 is pear-shaped to be commensurate in size with medial part 1310. In this manner, complementary engagement features of the medial part and the lateral part, 1312, 1356, line up for engagement between the two parts.

The glenoid implant may be varied in many ways. In some examples, the keel may be pear shaped when viewed in a medial to lateral direction but have a wider or narrower maximum width between ends of the keel. In some examples, the keel may be ovoid in shape, again, when viewed in a medial to lateral direction, such that it is symmetric about a single axis. In still further examples, the keel may be polygonal while having a tapered dimension in an inferior to superior direction. In some examples, a rim of the keel may have a lip or it may have a sharp edge. The keel may also have openings varying from the specific variations shown in the depicted embodiments. For instance, a side of the keel may have two separate openings therethrough, or the hollow part of keel extending along its depth may have two separate compartments.

In some examples, the lateral part may have a medial surface with a protruding central region that has planar surfaces thereon or has a surface that only includes part that is partially convex. The central region may be proportionally larger or smaller than what is shown in FIG. 7. Further, the height of the protrusion may be greater or lesser proportional to a size of the implant than that shown in FIG. 3. In some examples, the height of the protrusion will be 3 mm, a thickness of the lateral part in the central region, combined with a minimum distance between a plane of the peripheral region and a maximum depth of the articular surface.

In some examples, a medial part of the implant may exclude slots or may have a quantity of slots greater or lesser than three. In some examples, the keel may have no notches or have another structural feature in their place. In some examples, the central part of implants 200, 300 may be included as a part of another contemplated implant. In some examples, a single-component glenoid implant may include a keel such as keel 130. For instance, a monolithic single-component glenoid implant may be formed from molding the medial part to the lateral part.

In another aspect, the implant may form part of a kit. In one embodiment, a kit includes a set of at least two implants. In some examples, the set includes two or more implants of the same size. In some examples, the set includes at least two different sizes of implants. In some examples, the set includes some implants that are the same and at least one that is different. In some examples, a set may include two or more different types of implants. In another embodiment, a kit may include robotic cutting tools or a complete robot along with one or more implants. Any combination of implants may also be included in a single package or in separate packages which may be later brought together as a kit.

The kit may be varied in many ways. For example, it is contemplated that any combination of particular implants and tools as described herein may further include other tools or instruments not otherwise described as part of a kit. Some or all of the various combinations of elements of any contemplated kit may be included in a single package or distributed among multiple packages. In other examples, the kits contemplated herein may be accompanied by an instruction manual on how to perform one or more of the methods of using the contents of the kit.

In another aspect, the present disclosure relates to a method of assembly of an implant. In one embodiment, implant 100 as shown in FIG. 2 is assembled by bringing lateral part 150 to medial part 110 with medial surface 154 of the lateral part facing lateral surface 122 of the medial part. Engagement feature 156 is then snapped onto engagement feature 112, positioning an outer rim of lateral part 150 over the medial part, as shown, for example, in FIG. 3. In another embodiment, implant 200 is assembled in the same manner as implant 100 to bring central part 270 together with medial part 210. Then, lateral part 250 is slid over central part 270 by placing peripheral wall 256 over an outer surface of central part 270. In this manner, an interference fit is created between the parts. Similar methods of assembly may be employed for implants contemplated in the disclosure.

In another embodiment, implant 1000 as shown in FIG. 23 is assembled by advancing engagement portion 1052 of glenosphere 150 through opening 1042 in medial part 1010 to obtain an interference fit, e.g., via a Morse taper. A method of assembly of implant 1100 is similar, with an additional step of advancing fastener 1170 into opening 1146. In yet another embodiment, implant 1300 is assembled. Engagement features 1356 of lateral part 1350 are snap fit onto corresponding engagement feature 1312 of medial part 1310.

In yet another aspect, the present disclosure relates to a method of implantation of an implant in a joint. The joint may be a shoulder, but may be other joints in the body as well, such as a hip, knee or ankle. In one embodiment, a method of implanting a glenoid implant into a shoulder is as shown in FIGS. 28-31. The method may be performed autonomously or semi-autonomously with the assistance of a robotic manipulator for the implantation of the glenoid implant. Throughout the disclosure, the term "robotic manipulator" is used interchangeably with "robot." The robot may form part of a larger system (not shown) that includes a computer, memory, controller, inputs and outputs, and/or a navigation system, which may be interconnected with one another. The inputs may include a keyboard or other user interface and the output may include at least a display that outputs images and/or data associated with the three dimensional model and the surgical plan, among other information pertinent to the surgery. One function of the robot is to store data that relates to the location of various elements involved in the performance of the method. These include data for the location of the implant, the surface features on the implant, the cutting tool and the planned bone cuts. The robot may be configured to operate with haptic guidance, may be set up for connection to a cutting tool, such as a bur, and may be set up for connection to a rotatable driver for seating of the glenoid implant. Through the combination of the programmable robot and haptics, the system is configured to provide force feedback and visual guidance during surgery, as described in greater detail below.

Figure 28:
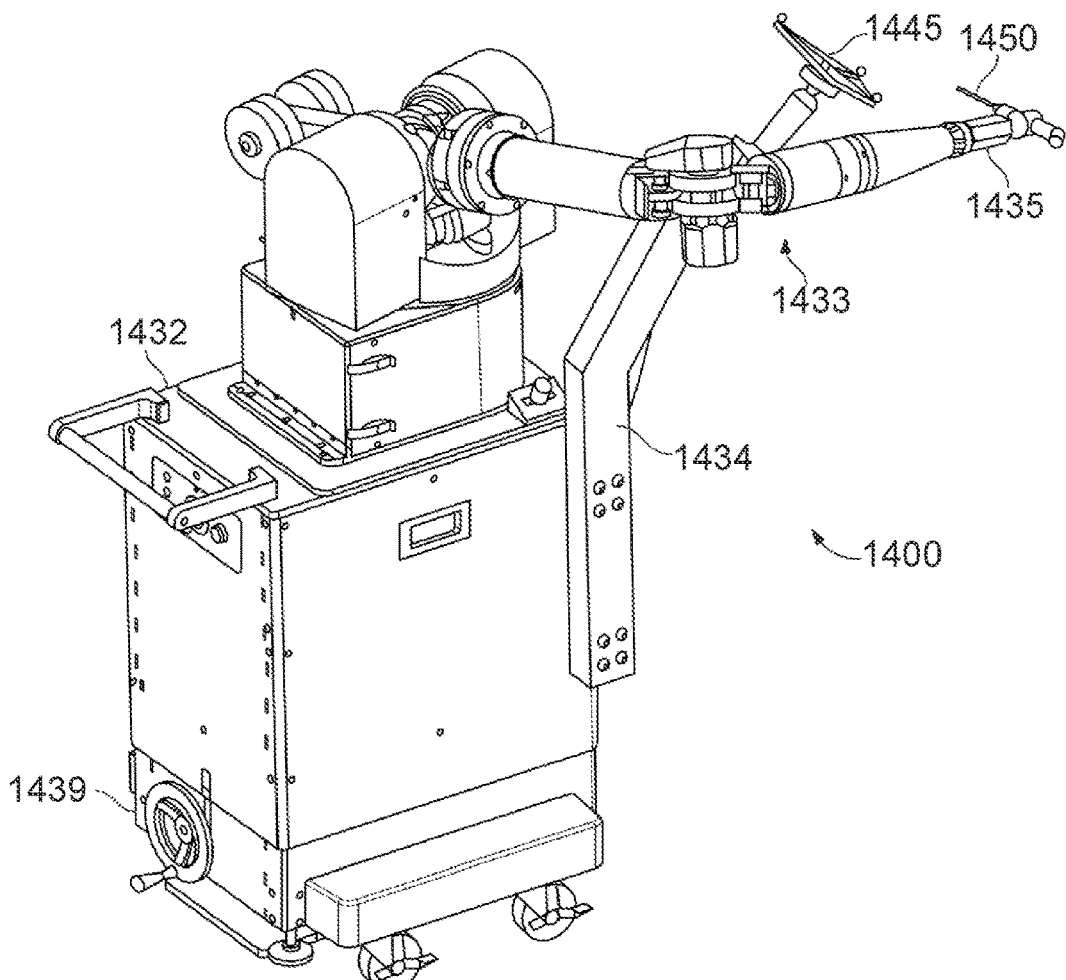
FIG. 28 is a perspective view of a robot with attached cutting tool according to one embodiment of the disclosure.

The robot with haptics may be as described in U.S. Pat. App. Pub. No. 2006/0142657 (the '657 Publication), hereby incorporated by reference herein in its entirety. The robot of the '657 Publication is shown in FIG. 28 as robot 1400 and includes a base 1432, platform 1439 and arms 1433, 1434 that extend from base 1432. Arm 1434 extends to a haptic device tracker 1445 while arm 1433 includes a plurality of linkages and extends to an end effector 1435 that connects to a tool. Here, the tool is a bur tool 1450, though in some arrangements, other tools may be attached. Another example of a robot is described in U.S. Pat. No. 7,831,292, hereby incorporated by reference herein in its entirety. In alternative approaches, the method may be fully automatic or may include certain steps performed manually by a user. The term "user" refers to an individual that performs the surgical method. This may include an operator of the robot or a surgeon, for example.

In some variations, the system used for the method may employ a robot that includes both a cutting instrument and imaging hardware. Such a robot is advantageous in that it streamlines workflow and reduces the need to move around the various parts of the system during the procedure and/or reduces the need for repeated registrations of one or more elements of the system. One example of such a robot is described in U.S. Pat. App. Pub. No. 2014/0188132, hereby incorporated by reference herein in its entirety.

With the anatomy registered, surgical planning, also referred to herein as planning, for the surgery surrounding shoulder 10 is performed. In short, planning involves establishment of the particular bone structure, including location, size and shape, to be cut with the robot. Because the glenoid implant is already manufactured at this stage and thus has a predetermined keel shape for engagement with bone, the dimensions of the glenoid implant are used as a guide to determine or confirm how the glenoid will be cut.

Figure 29:
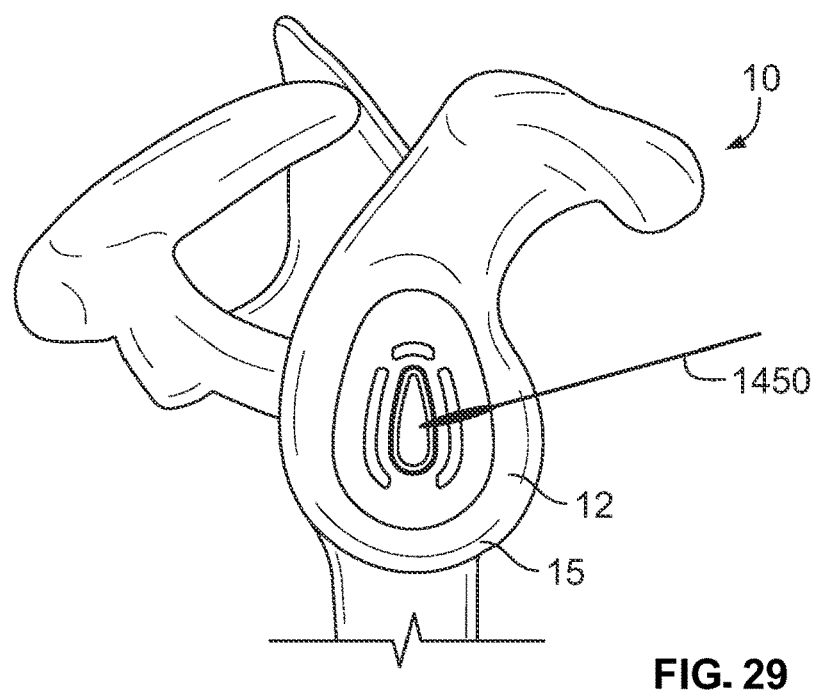
FIGS. 29-31 illustrate steps in a method of implantation of the glenoid implant of FIG. 1.
Figure 30:
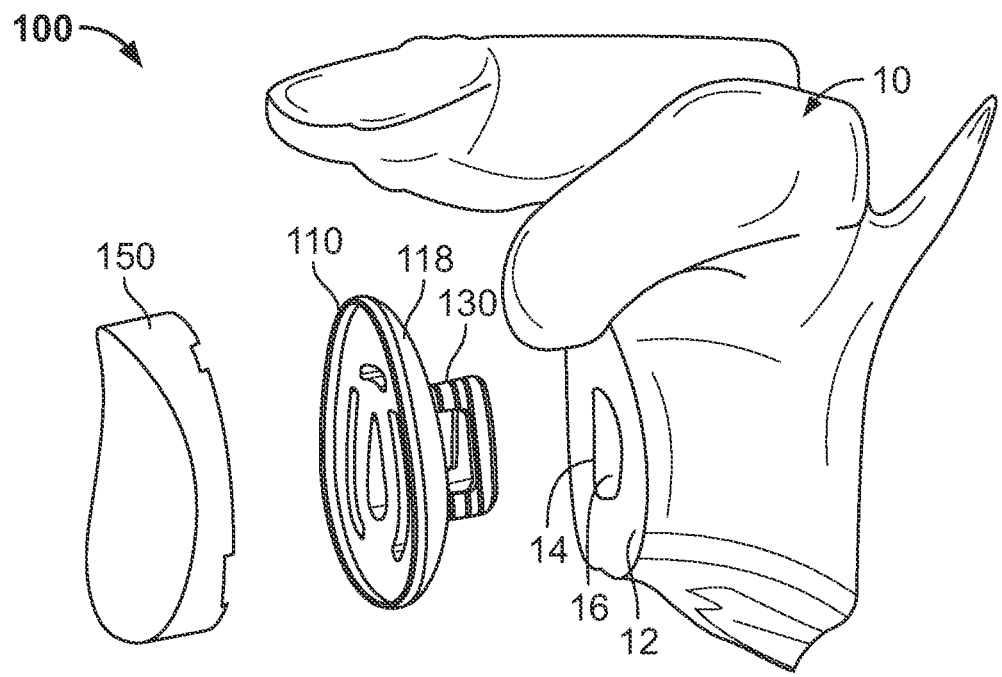
Figure 31:
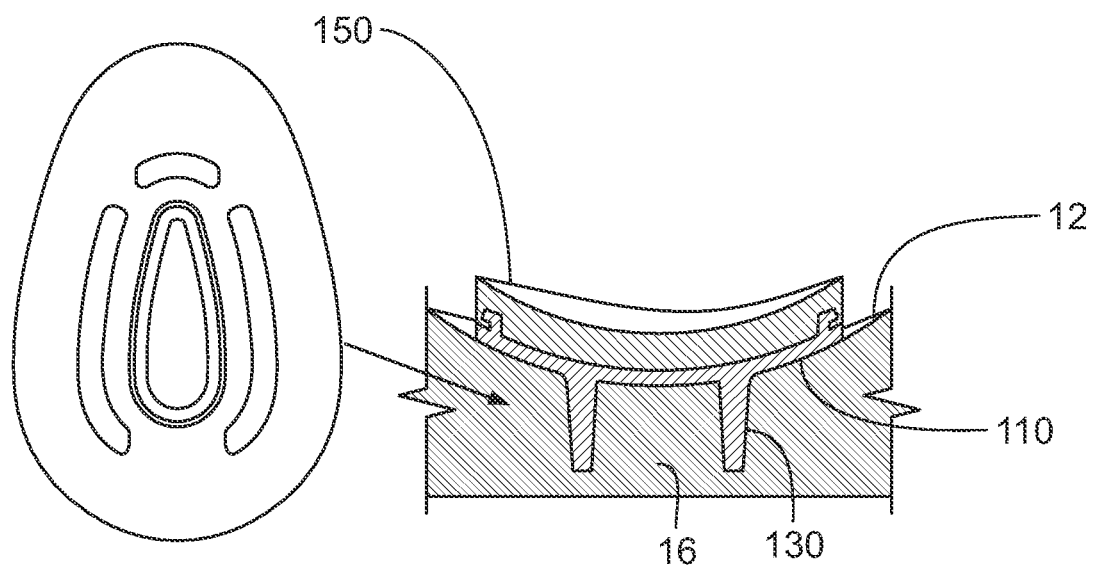

Turning to the details of the required bone cut or cuts, the robot may optionally be used to prepare an overall surface 12 of the glenoid to receive the medial part of the glenoid implant. The surface 12 is prepared as necessary to receive medial surface 118 of medial part 110. Such surface preparation is in accordance with known practices for shoulder replacement surgery and typically involves resection of bone to expose subchondral bone. Further, the bone surface is resected to refine its curvature to match that of medial surface 118 of medial part 110. Once any required glenoid surface preparation is complete, a deeper cut is made into the glenoid, as shown in FIGS. 29-31. In particular, a closed loop groove 14 is cut with a size and shape to receive keel 130. The groove is cut to a size so that an interference fit may be achieved when the keel is received in the groove. To render the surgical plan executable, data for the bone cuts is saved into the memory linked to the computer and incorporated into the three dimensional model described above.

With the precise identification of anatomical locations already in the model, this approach allows for very precise cutting of the bone so that when the implant is inserted into the glenoid, a close fit will result. In some variations of the method, the computer is used to generate boundary volumes for disposal of the implant into the resected bone as part of the planning process. In particular, the model may generate a range of acceptable cut volumes and/or cut paths in the bone that will allow for a satisfactory seating of the implant. Some examples describing the details of these planning steps are provided in U.S. Pat. App. Pub. No. 2017/0000562, hereby incorporated by reference herein in its entirety.

It should be appreciated that the exact dimensions of the planned cut may be varied based on results of an optional bone density review that may warrant deeper or shallower cuts. Some examples of how bone density of a particular patient may be used to optimize implant geometry are described in U.S. Pat. App. Pub. No. 2015/0119987, hereby incorporated by reference herein in its entirety. Similarly, the depth of the cuts may be slightly shallower to increase friction between the keel and the bone or deeper to reduce friction.

Turning to the operation of the robot and the bur, the robot, such as robot 1400, is connected to the controller and/or computer, along with the navigation system, to ensure data from the robot including the bur location is overlaid with the three dimensional model. The bur is then connected to the robot if not already connected. It should be appreciated that although the method is described with the use of a bur as a cutting tool, it is contemplated that other cutting tools may also be used. Through the connection of the robot to the overall system, advancement of the bur into the glenoid will be visible on the display showing the three dimensional model. As shown in FIG. 29, bur tool 1450, e.g., a ball bur tool, is then advanced to glenoid while the navigation system tracks the coordinates of the bur and relays such information to the computer to show a location of bur tool 1450 on the display that shows the three dimensional model. During this step, the model is viewable via the display and the surgical site is also viewable via direct visualization.

As referenced above, in some circumstances, when the robot is used to prepare the glenoid surface, the user references the cut plan on the model to guide bur 1450 to glenoid surface 12 to make the first cut, which is the initial surface cut that corresponds to the size and shape of the convex medial surface 118 of glenoid implant 100. This cut may be performed to expose subchondral bone on the glenoid. As the user performs the cut, the location of the bur tip is fed back to the computer and associated with the three-dimensional model information. The model has a predetermined cut depth based on the surgical plan programmed as noted above. As bur 1450 reaches the bounds of such depth or the outer limits of the cut near a perimeter 15 of the glenoid surface, the haptics of the robot generate increasing feedback, such as vibration, resistance, or a combination of the two, among others, to prevent the user from cutting outside of the predetermined limits of the planned cut volume. In this manner, the bone cut is precise and does not deviate from the surgical plan. Further detail regarding how haptics may be used to control cutting limits and volume are described in U.S. Pat. App. Pub. No. 2015/0080717, hereby incorporated by reference herein in its entirety. When this step is complete, glenoid surface 12 is sized and shaped to closely fit, e.g., be flush with a size and shape of the convex medial surface 118 of the implant.

However, prior to insertion of the implant onto the glenoid, a further cut to create the closed loop groove may be completed.

Similarly to the preparation of the glenoid surface 12 for receipt of the implant, bur tool 1450 is used to cut closed loop groove 14 in surface 12 in accordance with the three dimensional model parameters as established during the planning stage of the procedure described above. The application of bur tool 1450 to the glenoid surface to cut the grooves is shown in FIG. 29. The user directs the bur tool along the surface of the glenoid within a predetermined cut path for the tool to create closed loop groove 14. The cut path follows what may be described as a tear-drop shape as shown in FIG. 29. Through this cut, the remaining bone left intact interior to the groove, bone core 16, also has a tear-drop shape. The predetermined limits of the cut, including width, depth and cross-sectional shape, are programmed in the three dimensional model and are associated with coordinates that are continuously compared with coordinates of the bur tool. In this manner, when the bur tool reaches the limits of the predetermined cut path during use, the haptics of the robot provide increasing feedback in the same manner as occurs during execution of the first cut. Again, as with the first cut, the robot-assisted bur tool forms the groove with exacting tolerances as established through the three dimensional model. Upon completion of the cut required to create closed loop groove 14, the remaining glenoid is split into two regions, an outer surface region external to closed loop groove 14, and bone core 16 interior to closed loop groove 14, as shown in FIG. 30. Bone core 16 is undisturbed bone and preserves the original integrity of the bone to promote engagement between the implant and the bone.

At this juncture, the glenoid is ready to receive glenoid implant 100. Confirmation that the lateral part and the medial part of the implant are assembled is done prior to implantation, and assembly completed if required. Then, implant 100 is advanced onto the glenoid, and in particular, keel 130 is advanced into closed loop groove 14, as shown in FIGS. 30 and 31. This step may be done manually by the user or with the robot. When the robot is used, planning and controls as described above are utilized to obtain accurate placement. Further, the closed loop groove is sized with a high degree of accuracy such that once it receives keel 130, a secure fit should be expected with resistance to removal more than sufficient to hold the glenoid implant in place on the bone. As shown in FIG. 31, keel 130 occupies a volume of closed loop groove 14, with bone core 16 occupying the hollow interior of keel 130. Thus, one advantage of this method is that no separate bone substitute material, e.g., bone graft is required. This simplifies the method of implantation and renders it more efficient in terms of the time required for its performance. Further, without the need for bone graft, the possibilities for error during the method are reduced, another advantage. Once implantation is complete, bone ingrowth is promoted through the inclusion of porous material on medial surface 118.

The method of implantation described for glenoid implant 100 may also be performed to implant glenoid implants 200, 300, 400, 500, 600, 700, 800 shown in FIGS. 8-21. Such a method may be performed with the same steps as described above. For implant 600 in particular, use of such method may involve formation of a wider closed loop groove in the glenoid so that when the implant is inserted, there is space to flex the keel in order to allow the protrusion of the keel to snap into the outward facing step in the removed material. In another embodiment, a method of implantation of implant 600 shown in FIGS. 15 and 16 is performed as described above for implant 100, with additional steps as follows. When the glenoid is prepared, a central region 18 of the bone is removed and the robot is used to further remove an outward facing step 19 at a terminal depth of the cut, all shown in FIG. 16, where the implant is shown positioned within the space left subsequent to the removal of the bone material. This outward facing step may also be referred to as an undercut. When implant 600 is advanced onto the glenoid for implantation, keel 130 flexes inward to pass through the opening in the bone, and once the keel reaches the plan depth, lip 645 snaps into the undercut.

In another embodiment, a method of implantation of glenoid implant 100 involves preparation of an opening within the glenoid surface with a volume sufficient to receive keel such that when keel 130 is received in the bone, opening 142 within keel 130 remains unoccupied by bone. That is, a full volume of bone is removed for receipt of the keel and there is no bone core left in place once the cut in the glenoid is made. In this manner, such method may be performed with placement of bone graft in keel 130, then placement of keel 130 into the glenoid opening to position implant 100 in the implanted position. Bone graft may be received through graft opening 140 and opening 142. Because opening 140 includes two openings located on opposite sides of keel 130, this arrangement provides for bone ingrowth from three separate openings. Examples of bone graft that may be used include natural bone graft and a porous structure that acts as an allograft, such as a porous titanium. When natural bone graft is used, the humerus cut head may be used as a source. Once implanted, the porous material on medial surface 118 promotes bone ingrowth. Such a method may also be performed for the other contemplated implants, including glenoid implants 200, 300, 400, 500, 600, 700, 800.

Figure 32:
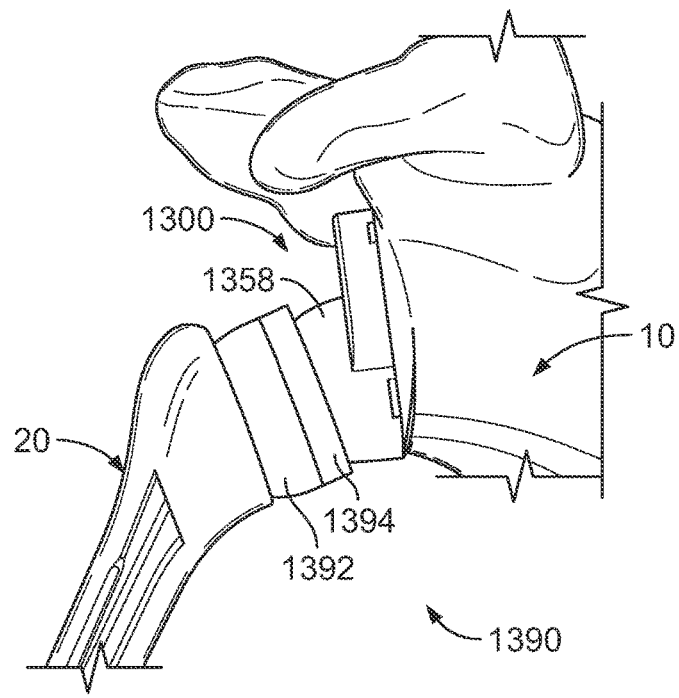
FIG. 32 is a front view of the glenoid implant of FIG. 27 implanted in a shoulder joint.

In yet another embodiment, a reverse shoulder implant with glenoid implant 1300 is implanted as part of an RSA. With keel 1330, implant 1300 may be implanted with methods that correspond to those described above for glenoid implant 100. A completed implantation, inclusive of reverse humeral implant 1390 and polymeric inner cup 1394, is shown in FIG. 32. In this configuration, contacting surfaces of the humeral part and the glenoid part are both polymeric.

Figure 33:
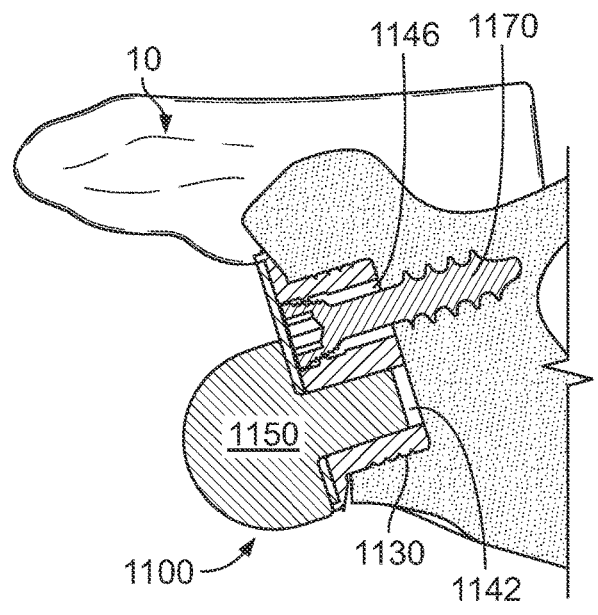
FIGS. 33 and 34 are side views of the glenoid implant of FIG. 24 implanted in a shoulder joint.
Figure 34:
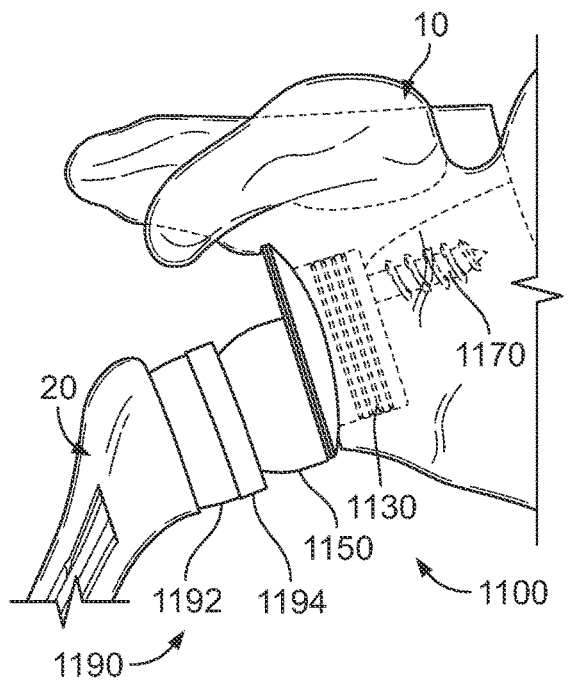

In yet another embodiment, another reverse shoulder implant is implanted into the shoulder as shown in FIGS. 33 and 34. A cavity is formed in the glenoid to receive keel 1130. The keel has notches 1144 to aid in engagement with the bone once the keel is in place. Additionally, a fastener element 1170 is receivable through opening 1146 in keel and thus may be advanced into bone to aid in the fixation of implant 1100 onto the glenoid. The fastener may be a locking and compression based screw. A complete assembly of the shoulder implant is shown in FIG. 34, with reverse humeral implant 1190 in the humerus, the humeral implant having a polymer articular surface and the glenosphere having a metallic articular surface for polymer-metal contact.

In another embodiment, a shoulder joint is prepared for implantation of glenoid implant 900 according to one of the methods described herein or other techniques known to those of ordinary skill in the art. Once a cavity is prepared in the glenoid that is sized for receipt of keel 930, blades 980A-B are rotated into the unlocked position shown in FIG. 22C. Then, the implant is advanced and otherwise impacted into place on the glenoid. Once the implant is in position on the bone, rotatable shaft 986 is actuated to rotate blades 980A-B into the locked position shown in FIG. 22D to provide additional engagement of the implant with the bone.

Although the embodiments described above and illustrated in the figures are directed to shoulder implants, the principles of creating a closed loop groove in solid bone to prepare such bone for the receipt of an implant, such as is described above for implants 100, 600, 700, for example, may be employed in a variety of joints. For example, a knee surgery may include a tibial implant with keel, the tibia being prepared with a closed loop resection to receive a hollow keel of the tibial implant. A similar approach may be adopted for a femoral implant at the knee. These principles may also be applied to methods of arthroplasty in the ankle or indeed other joints where a bone that receives an implant has sufficient structural integrity to benefit from having a "bone-core" left in place that will promote engagement with a keel. With appropriate modifications for shape, the implant may also be implanted in the spine.

In another aspect, the disclosure relates to a method of revision surgery to replace an existing glenoid implant. In one embodiment, glenoid 100 is replaced. An existing glenoid implant 100 is removed with a focus on removal of the keel through tool access provided by slots 120A-C. Such access allows for removal of bone ingrowth around the keel and for the preservation of the glenoid. Tools that may be used to perform such removal include osteotomes, for example. Once the existing implant is removed, a new implant is implanted according to a method as set forth elsewhere in the present disclosure or according to methods known to those of ordinary skill where other varieties of implants are used.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A glenoid implant comprising:
a body with an articulation surface and a bone facing surface; and
a keel having a depth extending from the bone facing surface to a free end of the keel remote from the bone facing surface, the keel having a first length and a first width both measured in a plane perpendicular to a direction of the depth, the first width being perpendicular to the first length,
wherein a first distance from an inferior end of the keel to a superior end of the keel defines the first length, a first portion of the keel extending from the inferior end to a first location and a second portion of the keel extending from the first location to the superior end, the first location being closer to the inferior end than the superior end, and
wherein the first width is measured at the first location, the keel having a width dimension along the first portion from the first location to the inferior end that tapers from the first location toward a single inferior-most location of the keel at the inferior end and the keel having a width dimension along the second portion from the first location to the superior end that tapers from the first location toward the superior end.

2. The glenoid implant of claim 1, wherein a first length of the body is defined by a second distance from an inferior end of the body to a superior end of the body, the body having a first width measured at a second location adjacent the inferior end of the body, the first width being perpendicular to the first length, and the body having a width dimension along a first portion of the body from the second location to the superior end of the body that tapers from the second location toward the superior end of the body.

3. The glenoid implant of claim 1, wherein the second portion of the keel is at least two times longer in a superior-inferior direction than the first portion of the keel.

4. The glenoid implant of claim 1, wherein the keel is hollow and defined by an enclosed wall, the enclosed wall having a superior part, an inferior part, a first side part and a second side part, the superior part having a first radius of curvature and the inferior part having a second radius of curvature greater than the first radius of curvature.

5. The glenoid implant of claim 2, wherein the keel has an ovoid shape in a cross-section cut at a third distance from the free end of the keel, the ovoid shape being symmetric about a single plane.

6. The glenoid implant of claim 1, wherein the keel is hollow and includes a first opening, a second opening and a third opening, the first opening at the free end of the keel, and the second and third openings being opposite one another on side surfaces of the keel in between the bone facing surface of the body and the free end.

7. The glenoid implant of claim 1, wherein the keel includes an outward facing protrusion around its perimeter at the free end.

8. The glenoid implant of claim 1, wherein the body includes a first peg and a second peg, each of the first and second pegs extending from the bone facing surface of the body.

9. The glenoid implant of claim 1, wherein the body includes a plurality of slots therethrough, each of the slots having an edge portion parallel to an outer surface of the keel.

10. The glenoid implant of claim 1, wherein the keel has an outer surface with a plurality of notches or protrusions thereon, each of the plurality of notches or protrusions having a length that extends around a perimeter of the keel and oriented perpendicular to the direction of the depth of the keel.

11. The glenoid implant of claim 1, wherein the keel includes a plurality of slits parallel to the direction of the depth of the keel, the inclusion of the plurality of slits increasing deformability of the keel.

12. The glenoid implant of claim 1, wherein the body includes a metallic medial part and a polymeric lateral part.

13. A glenoid implant comprising:
a medial part with a bone facing surface; and
a lateral part comprising:
a lateral facing surface, the lateral facing surface including a concave portion; and
a medial facing surface configured to couple to the medial part,
wherein the medial facing surface includes a peripheral region and a central region, the peripheral region separating an outer edge of the lateral part from the central region, and the central region having a protrusion relative to the peripheral region,
wherein the peripheral region abuts the central region along an inner edge, and
wherein the lateral part has a first thickness at the outer edge, a second thickness at the inner edge, and a third thickness in the central region, the second thickness being less than the first thickness, and the third thickness being no less than the second thickness and no greater than the first thickness.

14. The glenoid implant of claim 13, wherein the second thickness is in a range from 3 mm to 5 mm.

15. The glenoid implant of claim 13, wherein the medial facing surface of the lateral part has a first surface area coincident with the peripheral region and a second surface area coincident with the central region, the second surface area being larger than the first surface area.

16. The glenoid implant of claim 13, wherein the protrusion has a convex surface.

17. The glenoid implant of claim 16, wherein the convex surface of the protrusion has a radius in a range from 15 mm to 30 mm.

18. The glenoid implant of claim 13, wherein the protrusion includes a planar surface.

19. The glenoid implant of claim 13, wherein the concave portion of the lateral facing surface of the lateral part has a radius in a range from 15 mm to 30 mm.

* * * * *